US010893837B2

(12) United States Patent
Kohli et al.

(10) Patent No.: US 10,893,837 B2
(45) Date of Patent: *Jan. 19, 2021

(54) SIMULTANEOUS MULTI-PARAMETER PHYSIOLOGICAL MONITORING DEVICE WITH LOCAL AND REMOTE ANALYTICAL CAPABILITY

(71) Applicant: Cloud Dx, Inc., Brooklyn, NY (US)

(72) Inventors: Sandeep S. Kohli, Oakville (CA); David Widman, Oakville (CA); Sara Ross-Howe, Campbellville (CA); Robert Kaul, Brooklyn, NY (US)

(73) Assignee: Cloud Dx, Inc., Brooklyn, NY (US)

( * ) Notice: Subject to any disclaimer, the term of this patent is extended or adjusted under 35 U.S.C. 154(b) by 217 days.

This patent is subject to a terminal disclaimer.

(21) Appl. No.: 16/036,551

(22) Filed: Jul. 16, 2018

(65) Prior Publication Data

US 2018/0317859 A1 Nov. 8, 2018

Related U.S. Application Data

(63) Continuation-in-part of application No. 15/954,250, filed on Apr. 16, 2018, now Pat. No. 10,463,299, (Continued)

(51) Int. Cl.
*A61B 5/00* (2006.01)
*A61B 5/0404* (2006.01)
(Continued)

(52) U.S. Cl.
CPC ............ *A61B 5/746* (2013.01); *A61B 5/0022* (2013.01); *A61B 5/01* (2013.01); *A61B 5/022* (2013.01);
(Continued)

(58) Field of Classification Search
None
See application file for complete search history.

(56) References Cited

U.S. PATENT DOCUMENTS

| | | | | |
|---|---|---|---|---|
| 5,511,546 A | * | 4/1996 | Hon | A61B 5/6838 600/490 |
| 2002/0111777 A1 | * | 8/2002 | David | A61B 5/04085 702/189 |

(Continued)

*Primary Examiner* — Carl H Layno
*Assistant Examiner* — Manolis Pahakis
(74) *Attorney, Agent, or Firm* — Stephen E. Zweig

(57) ABSTRACT

Handheld medical diagnostic instrument that provides high time-resolution pulse waveforms associated with multiple parameters including blood pressure measurements, blood oxygen saturation levels, electrocardiograph (ECG) measurements, and temperature measurements. The device stores and analyzes the pulse waveforms simultaneously obtained from all tests, and thereby allows an unusually detailed view into the functioning of the user's cardiovascular heart-lung system. The device is designed for use by unskilled or semi-skilled users, thus enabling sophisticated cardiovascular measurements to be obtained in a home environment. Data from the device can be analyzed onboard, with local computerized devices, and/or with remote server based systems. The device or remote server may be configured to analyze this data according to various algorithms chosen by the physician to be most appropriate to that patient's particular medical condition (e.g. COPD patient algorithms). The device or remote server may be further configured to automatically provide alerts and drug recommendations.

10 Claims, 16 Drawing Sheets

Related U.S. Application Data which is a continuation-in-part of application No. 15/060,514, filed on Mar. 3, 2016, now Pat. No. 9,946,844, which is a continuation-in-part of application No. 14/186,151, filed on Feb. 21, 2014, now Pat. No. 10,022,053.

(60) Provisional application No. 62/138,377, filed on Mar. 25, 2015, provisional application No. 61/767,839, filed on Feb. 22, 2013.

(51) Int. Cl.

| | |
|---|---|
| *A61B 5/0402* | (2006.01) |
| *A61B 5/044* | (2006.01) |
| *A61B 5/0205* | (2006.01) |
| *A61B 5/021* | (2006.01) |
| *A61B 5/024* | (2006.01) |
| *A61B 5/01* | (2006.01) |
| *G16H 50/20* | (2018.01) |
| *A61B 5/1455* | (2006.01) |
| *A61B 5/022* | (2006.01) |
| *G16H 40/63* | (2018.01) |
| *A61B 5/0432* | (2006.01) |
| *A61B 5/0452* | (2006.01) |
| *A61B 5/08* | (2006.01) |

(52) U.S. Cl.
CPC ........ *A61B 5/0205* (2013.01); *A61B 5/02055* (2013.01); *A61B 5/02141* (2013.01); *A61B 5/02416* (2013.01); *A61B 5/02438* (2013.01); *A61B 5/044* (2013.01); *A61B 5/0404* (2013.01); *A61B 5/04028* (2013.01); *A61B 5/14551* (2013.01); *A61B 5/486* (2013.01); *A61B 5/6826* (2013.01); *A61B 5/7435* (2013.01); *G16H 40/63* (2018.01); *G16H 50/20* (2018.01); *A61B 5/0006* (2013.01); *A61B 5/0008* (2013.01); *A61B 5/02208* (2013.01); *A61B 5/02225* (2013.01); *A61B 5/02233* (2013.01); *A61B 5/02405* (2013.01); *A61B 5/0432* (2013.01); *A61B 5/0452* (2013.01); *A61B 5/0816* (2013.01); *A61B 5/14552* (2013.01); *A61B 5/4839* (2013.01); *A61B 5/7278* (2013.01); *A61B 5/7285* (2013.01)

(56) References Cited

U.S. PATENT DOCUMENTS

| | | | |
|---|---|---|---|
| 2006/0217616 A1* | 9/2006 | Kuchler | A61B 5/02416 600/485 |
| 2008/0221404 A1* | 9/2008 | Tso | A61B 5/4872 600/301 |
| 2008/0221930 A1* | 9/2008 | Wekell | G06F 19/36 705/3 |
| 2014/0012146 A1* | 1/2014 | Fukuda | A61B 5/02125 600/485 |
| 2014/0031638 A1* | 1/2014 | Jung | A61B 5/024 600/301 |
| 2014/0243612 A1* | 8/2014 | Li | A61B 5/02233 600/301 |
| 2016/0270668 A1* | 9/2016 | Gil | A61B 5/681 |
| 2017/0319082 A1* | 11/2017 | Sayme | A61B 5/04017 |
| 2018/0020937 A1* | 1/2018 | Chou | A61B 5/0408 600/301 |
| 2018/0317859 A1* | 11/2018 | Kohli | A61B 5/022 |
| 2020/0029839 A1* | 1/2020 | Tseng | A61B 5/02438 |

\* cited by examiner

SIMULTANEOUS MULTI-PARAMETER PHYSIOLOGICAL MONITORING DEVICE WITH LOCAL AND REMOTE ANALYTICAL CAPABILITY

CROSS REFERENCE TO RELATED APPLICATIONS

This application is a continuation in part of U.S. patent application Ser. No. 14/186,151, filed Feb. 21, 2014; application Ser. No. 14/186,151 claimed the priority benefit of U.S. provisional patent application 61/767,839 "SIMULTANEOUS MULTI-PARAMETER PHYSIOLOGICAL MONITORING DEVICE WITH DUAL LOCAL AND REMOTE ANALYTICAL CAPABILITY", filed Feb. 22, 2013, which issued as U.S. Pat. No. 10,022,053; this application is also a continuation in part of U.S. patent application Ser. No. 15/954,250, "SYSTEMS AND METHODS FOR MONITORING MEDICATION EFFECTIVENESS", filed Apr. 16, 2018, which issued as U.S. Pat. No. 10,463,299; application Ser. No. 15/954,250 was a continuation in part of application Ser. No. 15/060,514, filed Mar. 3, 2016, now U.S. Pat. No. 9,946,844 issued Apr. 17, 2018; application Ser. No. 15/060,514 claimed the priority benefit of U.S. provisional application 62/138,377, "COMPREHENSIVE BODY VITAL SIGN MONITORING SYSTEM WITH NECK AND EAR MOUNTED DEVICE, filed Mar. 25, 2015; application Ser. No. 15/050,514 was also a continuation in part of U.S. patent application Ser. No. 14/186,151 "SIMULTANEOUS MULTI-PARAMETER PHYSIOLOGICAL MONITORING DEVICE WITH LOCAL AND REMOTE ANALYTICAL CAPABILITY", filed Feb. 21, 2014; application Ser. No. 14/186,151 in turn claimed the priority benefit of U.S. provisional application 61/767, 839 "SIMULTANEOUS MULTI-PARAMETER PHYSIOLOGICAL MONITORING DEVICE WITH DUAL LOCAL AND REMOTE ANALYTICAL CAPABILITY", filed Feb. 22, 2013; the entire contents of all of these applications are incorporated herein by reference in their entirety.

BACKGROUND OF THE INVENTION

Field of the Invention

This invention is in the field of medical devices to monitor blood pressure, blood oxygen levels, and obtain electrocardiograms. In particular the invention is in the field of handheld medical device designed for easy use by unskilled or semi-skilled patients and healthcare professionals.

Description of the Related Art

The human cardiovascular system is a complex system involving the heart, lungs, arteries, veins and other body components. The human heart itself can be viewed as an electrically triggered four-chamber pump. The right atrium receives deoxygenated blood (generally more blue in color) from the veins, passes the blood to the right ventricle, where the blood is pumped to the lungs. At the lungs, the blood becomes oxygenated (and also changes to a red color depending upon how much oxygen has been absorbed).

The left atrium receives oxygenated blood from the lungs, and passes this oxygenated blood to the left ventricle, which in turn sends oxygenated blood to the body via various arteries. During each heartbeat, usually in response to various electrical pulses (which can be monitored using electrodes and electrocardiogram type methods) various pulsatile sounds are generated (called Korotkoff sounds when used in a cuff-type blood pressure monitoring context), and various pulsatile changes in blood pressure also occur. For example, when the left ventricle is pushing oxygenated blood to the body, blood pressure is higher (systolic blood pressure), and in between heartbeats, when the heart is momentarily resting, the blood pressure is lower (diastolic blood pressure), and these pressure measurements vary according to the patient's pulse rate (typically between about 30 to 200 times per minute).

Various medical abnormalities can alter this process. For example, some medical conditions may cause the heart to beat irregularly (cardiac arrhythmia), and such cardiac arrhythmias are often of high medical concern. Blood pressure may be too high or too low. Due to either cardiac problems, lung problems, or a combination of the two, blood may not be sufficiently oxygenated as it passes through the lungs. Indeed in some diseases, such as chronic obstructive pulmonary disease (COPD), all aspects of the cardiovascular system may be gravely damaged.

Not surprisingly, given how fundamental a well performing cardiovascular system is to human health, various methods of monitoring different aspects of the human cardiovascular system have been developed.

Thus if a heart is receiving abnormal electrical signals, which can be diagnosed by electrodes and electrocardiographic (ECG) methods, the heart muscle may contract abnormally. This abnormal heart muscle contraction may in turn generate an abnormal pulse with characteristic sounds and characteristic changes in blood pressure. These pulse signals may be monitored by traditional sphygmomanometer type blood pressure monitors, which apply pressure to a portion of the body, and monitor the Korotkoff sounds with a stethoscope as a function of the amount of applied pressure. The pulse signals may also be monitored by more recently developed oscillometric methods, where oscillating pressure measurements at various cuff pressure levels can be automatically analyzed according to various algorithms, and pulse results produced. The variation in blood color (light absorption spectra) as a function of blood oxygen levels (saturation) can also be monitored by various types of pulse oximeter measurements.

Previous work in these fields includes Uemura, U.S. Pat. Nos. 4,262,674 and 4,484,584; Taniguchi, U.S. Pat. No. 4,566,464, Shimazu, U.S. Pat. No. 5,680,867, Swearington, U.S. Pat. No. 4,263,918, Amano U.S. Pat. No. 6,095,984, Forstner U.S. Pat. No. 6,485,429, and Muradina, US patent publications 20080077435 and 20120330675; the complete contents of these applications are incorporated herein by reference.

The role of telemedicine in assisting care for COPD was recently reviewed in 2012 article by McLean et. al., ("*Telehealthcare for chronic obstructive pulmonary disease (Review)*", *The Cochrane Library* 2012, issue 8, published by John Wiley & Sons, Ltd).

Methods to derive respiratory rate from pulse oximeter data was discussed by Addison et. al., ("*Developing an algorithm for pulse oximetry derived respiratory rate (RRoxi): a healthy volunteer study, J. Clin. Monit. Comput* (2012) 26: 45-51), and by Leonard et. al., "Standard pulse oximeters can be used to monitor respiratory rate", Emerg Med J 2003, 524-525.

Oscillometric methods to measure systolic and diastolic blood pressure were discussed in Babbs, ("*Oscillometric measurement of systolic and diastolic blood pressures vali-* dated in a physiologic mathematical model", *Biomedical Engineering Online* 2012 11; 56.)

BRIEF SUMMARY OF THE INVENTION

For critically ill patients in intensive care settings, who are typically under the direct supervision of one or more physicians, it is now standard practice to monitor a number of different cardiovascular parameters simultaneously. However in settings outside of hospital intensive care units, such as home settings, such multi-parameter measurements are rarely, if ever, done.

Here, because some embodiments of the invention may be designed for home use by unskilled patient/users, the terms "patient" and "user" will often be used interchangeably.

The invention is based, in part, on the insight that although wrist and arm based blood pressure monitors are simple to use, and thus are often preferred by patients in a home monitoring situation, merely monitoring only blood pressure during a routine blood pressure monitoring session represents a wasted opportunity. To more fully utilize this time window of patient interaction with a medical diagnostic device, a more capable device that is also capable of recording additional relevant patient physiological information, such as patient electrocardiogram (ECG) and blood oxygen levels, as well as other parameters such as temperature and breathing rate would be also desirable. It would further be desirable to provide an ability to extensively analyze the data remotely, as well as to easily relay the data to healthcare providers, caregivers, and other decision makers.

Blood oxygen levels can be produced by, for example, using various types of clip on finger pulse oximeters. These clip on finger pulse oximeters operate by shining light of various wavelengths through the patient's fingernail or other part of the patient's finger, often at wavelengths around 660 nm or infra-red wavelengths around 905-940 nm, where the color of blood hemoglobin is highly variable according to the degree of oxygenation of the blood, and other reference wavelengths, such as 590, and/or 805 nm, where the color of blood hemoglobin remains more constant regardless of degree of oxygenation. After passing through at least part of the finger or fingernail, the light is then detected with a photodetector, analyzed using a computer processor, and blood oxygen level computed.

By contrast, electrocardiogram (ECG) measurements are usually difficult and cumbersome to obtain, because most medical grade ECG measurements require that multiple electrode leads (e.g. 12 or more leads) be placed (usually taped) around various areas of the patient's body. In addition to providing additional medically useful information, multiple leads can also reduce noise and improve the quality of the signal.

The invention is based in part, on the insight that there may be advantages to abandoning the medical prejudice in favor of high numbers of electrode leads for ECG applications. If ECG methods using a smaller number of leads are used (e.g. two or more electrodes, but less than 13 electrodes), such as one reference lead attached to the patient's finger, and another lead attached to the patients opposite hand, then the same clip-on finger pulse oximeter used to obtain a blood oxygen measurement could also be used to hold a clip on lead for a simple ECG measurement as well.

The invention is further based on the insight that the box or chassis used to hold the working components (e.g. air pump, microprocessor, battery, optional chassis mounted display) of a portable handheld wrist or arm blood pressure sensor can also be used to provide at least one reference electrode(s) for an ECG measuring device. The invention is further based on the insight that it would be useful to combine, in one basic handheld instrument (or device), the functions of a wrist or arm mounted blood pressure monitor (with inflation cuff); with a clip on finger blood pulse oximeter that also includes at least a first ECG electrode lead and optional temperature sensor. The invention is further based on the insight that it would be useful to position at least one other ECG electrode lead on the surface of the handheld device. Such a device would enable the patient or user to hold the device chassis in one hand, thus establishing an ECG electrode connection. The wrist or arm blood pressure monitoring cuff can be mounted on the wrist of the user's other hand. The clip-on combination blood oximeter/electrode (with optional temperature sensor) can be placed over the user's finger. The system can be further configured with a microprocessor that directs the device to sense the status of the various sensors multiple times per second while pressure is automatically applied to the inflation cuff, and store the results in memory.

Such a device would provide a wealth of data, such as synchronized blood pressure cuff obtained pulse waveforms, oximeter obtained pulse waveforms, and ECG waveforms while pressure was progressively applied and then released on the patient's wrist. This in turn would generate a large amount of physiologically relevant patient data that could then be used to monitor for the presence or progression of various diseases, in particular various cardiovascular diseases and lung diseases, such as COPD.

Note that these various types of pulse waveforms are occasionally also called "pulse waves". Such "pulse waves" can denote various different types of pulse related waveforms, such as oscillometric blood pressure waveforms, ECG pulse waveforms, pulse oximeter pulse waveforms, and the like. Here the pulse waveforms or pulse waves denote the shape of the waveform as a function of time. From the shape of the waveforms as a function of time, other types of information, such as pulse wave velocity (PWV) or pulse transit time (PTT) and other types of measurements, such as assessments of cardiac function, and the like, can be obtained.

Note also that because the present system is designed to measure different types of pulse waveforms simultaneously, these different types of pulse waveforms or pulse waves are thus also synchronized in time. That is, the system microprocessor or processor is configured to keep track of the times in which the various types of pulse waves or pulse waveforms are received, at least relative to each other, so that, for example, the relative time position of a peak or trough of an oscillometric blood pressure pulse wave can be compared to the peak or trough of an ECG pulse wave at the same time interval, and these turn can be compared to the peak or trough of a pulse oximeter pulse wave at the same time interval. As it turns out, the peaks or troughs of the different types of pulse waves (pulse waveforms) are not entirely synchronized with each other in time, and the time differences between the detection of the various peaks or troughs, as well as variations in intensity of the various peaks or troughs, can convey important physiological and medical information regarding the health of a patient, as well as the effect of various therapeutic drugs upon the patient as well.

The invention is also based, in part, on the insight that although small standalone diagnostic instruments are often most convenient to use for rapid point of care acquisition of information, often the onboard analytical and data display capabilities of such devices are sub-optimal. Thus providing standalone capable medical diagnostic devices with the capability of interfacing with other computer systems with additional analytical and display software capability, either through local and more capable computerized devices (e.g. local personal computers, tablet computers, and the like) or remotely (e.g. through various server systems) would be particularly desirable for multi-parameter monitoring devices, such as the invention's combined device.

The remote server approach has some additional advantages as well. In addition to providing additional computing capability, a remote server can provide a means for providing a higher level of quality control (QA) in a home-monitoring situation. Traditionally, Q/A has been difficult for home-based monitoring situations. However remote servers can use the person's historic data, population data from other users, and knowledge of the characteristics of that device and the population of similar type devices for purposes of improved raw-data validation, as well as providing improved user guidance as to best modes of using the device, and best times for data collection.

DETAILED DESCRIPTION OF THE INVENTION

Figure 1:
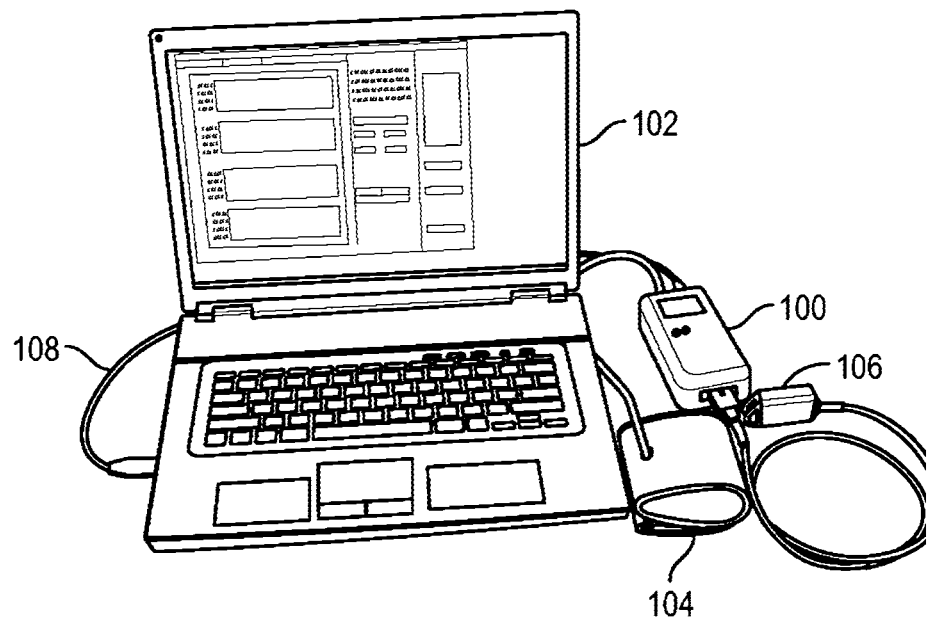
FIG. 1 shows the multi-parameter monitoring device operating in computer accessory mode, where the device may be controlled by another computerized device through a data connection such as a USB or Bluetooth™ connection, and in some embodiments also obtain power through the other computerized device. Both a prototype design, as well as a more refined version of the device, are shown.
Figure 1:
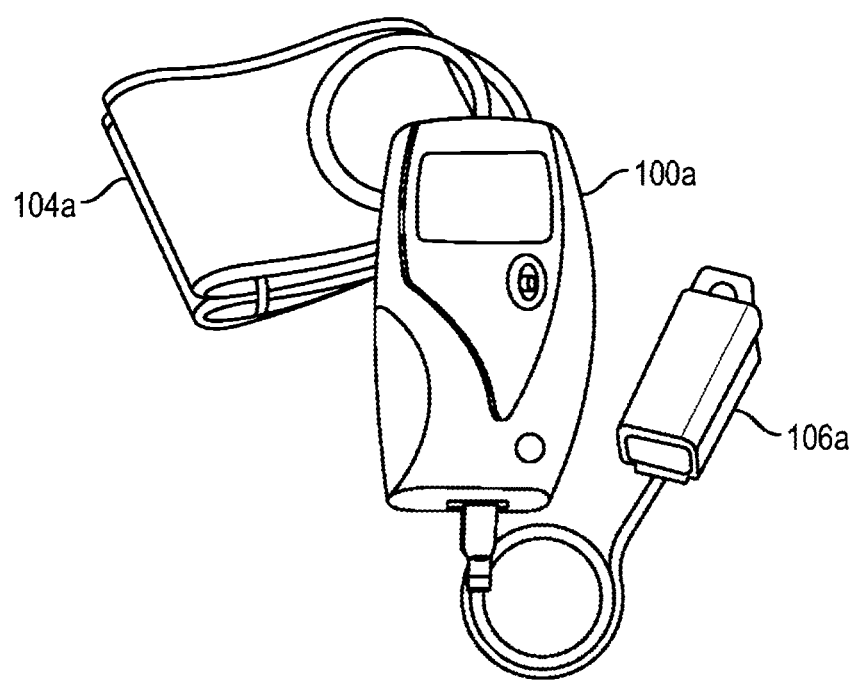

In one embodiment, the invention may be a portable handheld device and method for simultaneously monitoring pulse waveforms indicative of blood pressure, blood oxygen levels, and electrocardiogram signals. This device will generally comprise a handheld base unit controlled by at least one microprocessor or microcontroller, suitable control software (often stored in flash memory), additional memory (e.g. RAM, additional Flash memory, which may also be used to store data accumulated by the device), an optional built-in display such as an LCD display, and various user control inputs such as various buttons, switches and the like.

The microprocessor or microcontroller will generally comprise, or at least be connected to, a plurality of ports to drive various external devices to be discussed, as well as various inputs to either directly digitize various input analog signals, or else accept analog inputs in digital form via various external A/D converters. More specifically, by connecting an external device to one or more of such ports, the microprocessor or microcontroller can then drive that particular external device.

In some embodiments the optional built-in display may be a touch-sensitive display, in which case at least some of the various user control inputs may be implemented via the optional, built-in, touch sensitive display.

Although in some embodiments, the device may be configured for use by unskilled users such as in a home setting, the device will also frequently be configured for professional healthcare worker use as well.

The handheld base unit will generally comprise one or more air pumps and valves for driving a pneumatic blood pressure monitoring cuff (e.g. a sphygmomanometer), as well at least one detector, such as a microphone or pressure sensor to monitor pulse input (e.g. pulse sounds or pulse pressure differences) from the blood pressure monitoring cuff (usually carried by hollow tubing). This pneumatic blood pressure monitoring cuff (e.g. cuff, external cuff) will connect to the handheld base unit via intermediate tubing and via a hole or port in the handheld base unit (external cuff port).

The handheld base unit will often further comprise at least one first ECG electrode(s) mounted on the external chassis of the handheld base unit (302). This first ECG electrode will generally be placed in an area of the external chassis that would be a natural location for the patient (i.e. person being monitored) to hold the unit by one hand. Thus this first ECG electrode is intended to directly touch the patient's hand while the patient is holding the handheld base unit. In some embodiments, a temperature sensor, configured to measure the temperature of the user's hand, may also be positioned on or below this first ECG electrode.

The interior of the handheld base unit will also contain electrical circuitry for an ECG amplifier, as well as an electrical ECG-oximeter port to receive input from a second ECG electrode mounted on the interior of an external finger mounted combination pulse-oximeter-ECG electrode device. This will be discussed in more detail shortly. This external finger-mounted combination pulse-oximeter-ECG electrode device can be used by the system, in conjunction with the at least one first ECG electrode on the exterior of the device housing, to obtain electrocardiogram pulse wave information.

Other electrodes, such as one or more chest mounted electrodes, may also be used as desired in order to obtain good ECG data.

Note that in a preferred embodiment, the finger mounted pulse-oximeter-ECG electrode will be mounted on a digit of the patient (i.e. finger, toe) that is different from the hand that the patient is using to hold the external chassis of the handheld base unit. Generally, the electrical path should at least in part cross the patient's heart.

The interior of the handheld base unit will also contain electrical circuitry to drive a plurality of finger pulse oximeter light sources at a plurality of wavelengths, and to receive photodetector signals from, the oximeter portion of the combination external finger mounted pulse-oximeter-ECG electrode device. The interior of the handheld base unit will optionally also contain electrical circuitry to read the status of at least one temperature sensor mounted either on the external finger-mounted pulse-oximeter-ECG electrode device, or on the handheld base unit.

The device software may be configured so that when a blood pressure monitoring cuff is temporarily or permanently plugged into the device's external cuff port (and then placed around the limb of a patient, such as around the wrist of the patient's arm), and the device's external finger mounted combination pulse-oximeter-ECG electrode device is placed around the digit of the patient (ideally a finger or thumb of the hand opposite to the hand of the patient that is holding the chassis and first electrode of the handheld device), the device will then apply (via the microprocessor or microcontroller at least one air pump and valve) varying amounts of air pressure to the cuff, usually by way of a hollow tube connecting the cuff to the device base unit.

Put alternatively, in this context, "around the limb of a patient" means that the blood pressure monitoring cuff can be viewed as being located or situated on the user's limb so as to surround a circumference of the user's limb.

The device's blood pressure microphone or other sensor (e.g. a pressure sensor) will typically either listen to patient pulse sounds, or more commonly (using oscillometric methods) measure pressure differences traveling over the hollow tube. This sensor will thus obtain pulse wave information as a function of applied cuff air pressure. Alternatively, the device may contain a microphone (or other sensor such as a pressure sensor) mounted as part of the pneumatic blood pressure cuff, and obtain data by this method.

Generally the pulse sounds/pressure fluctuations vary as a function of applied cuff pressure, and patient blood pressure. When patients with higher blood pressure are tested, the pulse sounds or pulse pressure fluctuations to persist at higher cuff pressures. By contrast for patients with lower blood pressure, the pulse sounds or pulse pressure fluctuations will be more diminished at higher cuff pressures. This method can not only be used to obtain blood pressure (i.e. systolic, diastolic readings), but additionally, the shape of the waveforms can also be monitored, typically at least several times a second, to obtain further information pertaining to the presence of various cardiac arrhythmias and other medical disorders as well.

As previously discussed, blood pressure information may be obtained by either automatic (e.g. microprocessor performed) analysis of the Korotkoff sounds or by more modern oscillometric methods. In a preferred mode, oscillometric methods will be used. These methods may operate according to the algorithms of Babbs, ("*Oscillometric measurement of systolic and diastolic blood pressures validated in a physiologic mathematical model*", Biomedical Engineering Online 2012 11; 56.), or by alternative algorithms.

Examples of how such waveforms (often obtained using oscillometric methods) may be used to diagnose cardiac disease and arrhythmias are discussed in more detail in in the Nov. 9, 2011 Biosign publication "*Arrhythmias The UFIT® acquired pulse waveform is a simple and informative mode of screening for arrhythmias, as well as a longitudinal tool for monitoring changes in the rhythm of the pulse*", and the Nov. 25, 2011 Biosign "*ANSI/AAMI SP*10 *Report The UFIT® measurement of blood pressure meets all performance requirements of ANSI/AAMI SP*10:2002 *as an automated sphygmomanometer.*", the contents of which are provided as references and the contents of which are also incorporated herein by reference.

The device may also be configured (e.g. via software and microprocessor/microcontroller control) to drive the external combination finger pulse-oximeter-ECG electrode device at a plurality of wavelengths, and obtain blood hemoglobin absorbance information as a function of wavelength and as a function of pulse wave. This method works because hemoglobin is known to change its relative absorbance at certain wavelengths very strongly as a function of degree of oxygenation, but at other wavelengths the absorbance of hemoglobin varies little or at all depending upon degree of oxygenation. At the same time, depending upon the pulse cycle, at some pulse stages such as during the contraction stage, the capillaries of the skin and tissues are filled with red-cell containing blood (where the hemoglobin is stored), while at other stages of the pulse cycle, such as during the relaxation stage, there is relatively little red blood cells and hemoglobin present, thus allowing background absorbance due to other body tissues to be subtracted from the overall signal. The net result is that by suitable analysis, both another type of pulse wave reading is obtained, and additionally the degree of oxygenation of the blood can also be determined.

This degree of oxygenation differs slightly according to if the patient has just inhaled or just exhaled, and thus breathing rate information may also be extracted by automated analysis pulse oximeter data as well.

An additional advantage of combining finger based blood oximeter data with a wrist or arm mounted blood pressure cuff type blood pressure monitor is that the combination of the two different modes of collecting data can potentially provide more accurate systolic and diastolic blood pressure measurements. This is because during the time when the blood pressure cuff is inflated to the maximum extent to measure the systolic phase of the pulse (maximum contraction), the pulse pressure wave detected by the blood pressure monitor is at a maximum, and at the same time the smallest quantity of blood, and likely more deoxygenated blood is received at the user's finger. This shows up as local pulse minimums in the hemoglobin and oxyhemoglobin oximeter blood absorption channels.

By contrast, during the time when the blood pressure cuff is deflating in order to measure the resting phase of the heartbeat (diastolic phase), the pressure wave detected by the blood pressure monitor is at a minimum, while both a larger amount of blood, and also generally more oxygenated blood, is received at the user's finger. This shows up as greater signals in the hemoglobin and oxyhemoglobin oximeter blood absorption channels.

Thus when the pressure in the cuff is greater than the patent's systolic blood pressure, the blood flow to the patient's palm is cut-off and, thus the finger mounted pulse-oximeter will not register or detect any pulses. However when the pressure in the cuff falls below the patient's systolic blood pressure, but is still greater than the patient's diastolic blood pressure, there will be intermittent blood flow to the patient's fingers, producing an abnormal set of pulse waveforms. This intermittent blood flow can be detected by the finger mounted pulse-oximeter. In general, the pulse detected by the finger mounted pulse-oximeter will start to more fully resemble a normal pulse when the pressure in the cuff falls below the patient's diastolic pressure.

Thus, regardless of if the blood pressure cuff is operating by the oscillometric blood pressure method by detecting pressure sensor changes, or if the blood pressure cuff is operating by analysis of Korotkoff sounds using a microphone type sensor, any errors in the blood pressure' cuff assessment of systolic and diastolic blood pressure can, at least to some extent be either detected, or preferably even corrected, by use of blood oximeter data.

Thus in some embodiments, either the device's software and processor (or the remote server processor and software) may be further configured to use the blood hemoglobin absorbance information as a function of wavelength and as a function of pulse wave to improve the accuracy of blood pressure monitoring information obtained from the blood pressure monitoring cuff.

According to the invention, the device is also configured to monitor electrical signals from a first ECG electrode mounted on the external chassis of the handheld base unit, and a second ECG electrode mounted on the interior of the device's external, finger-mounted, combination pulse oximeter and ECG electrode.

This thus allows the device to obtain electrocardiogram electrical pulse wave information as well, usually during the same time that the cuff is operating producing its type of audio pulse wave data, and the oximeter is obtaining blood oxygen levels and optical pulse wave data. The net result is a "three dimensional" electrical/audio/optical analysis of the same pulse waves. That is, same heart beats can be analyzed from a blood pressure standpoint, a blood oxygen standpoint, and an ECG electrical activity standpoint. This technique thus provides a unique perspective on patient cardiovascular information. Critically, due to the portability and ease of use of the device, this data can be obtained in a much broader range of settings (e.g. clinic, home, travel) settings than otherwise was previously feasible. This facilitates both higher frequency monitoring, as well a better monitoring during times that the patient may be experiencing some distress at home.

In a preferred embodiment, the device software is configured to direct the device's microprocessor or microcontroller to store (in either local or remote memory), either the direct sensor readings, or alternatively or additionally variously mathematically processed versions these readings. Thus on a simultaneous or near-simultaneous basis, blood pressure monitoring pulse wave information (data), data from the external, finger mounted, combination pulse-oximeter-ECG electrode blood oxygen levels (e.g. device blood hemoglobin absorbance information as a function of wavelength pulse wave information), and various electrocardiogram pulse wave information useful for detecting cardiac arrhythmias and other problems can be obtained.

Although, in many embodiments, the device may be configured to analyze the data internally using its onboard microprocessor/controller or onboard software, in a preferred embodiment, the device may also be configured provide these various types of data, along with engineering data such as device air pressure information, light source driving timing data, amplifier settings, what part of the body the various sensors are connected to, and the like, to an external computerized device or remote server (often with more sophisticated data analysis capability) via a wired, wireless, or optical communications port.

This external computerized device or remote server, which often may have more data analysis and/or display capability than the device itself, may in turn be configured to analyze this data, generate medically useful graphs of this data, and also report on medically useful parameters such as various mathematically computed blood pressure, blood oxygen level, and ECG results.

As will be discussed, the remote server approach is also particularly useful because it can give the physician more options to customize the automated data analysis and medical recommendation process to the needs of individual patients. The remote server approach can also be particularly useful for home monitoring applications, because the remote server can also provide improved quality assurance (Q/A) and control. This is particularly important for home monitoring situations, where the chances of error may be higher.

The external computerized device may be a laptop computer connected to the invention using a wired USB (Universal Serial Bus) connection, as is shown in FIG. 1. However in a preferred mode, the external computerized device may be a smaller handheld device, such as a smartphone or tablet computer, connecting to the invention using a wireless Bluetooth™ connection. This smaller handheld device may in turn connect to remote servers using WiFi or direct cellular (e.g. 3G, 4G) type wireless connections. In some embodiments, some data analysis may be done directly on the local external computerized device, while more extensive data analysis, which may be done by various physician selected algorithms, may be done on the remote servers, and then relayed to the physician or other healthcare provider.

EXAMPLES

One embodiment of the device is exemplified by the UFIT-max system, presently in development. The UFIT-max is a portable vital sign monitoring device that integrates automatic blood pressure monitor, single lead ECG and pulse oximeter functions, and optional body temperature sensor into a personal digital accessory (PDA) (e.g. handheld) sized box.

Figure 2:
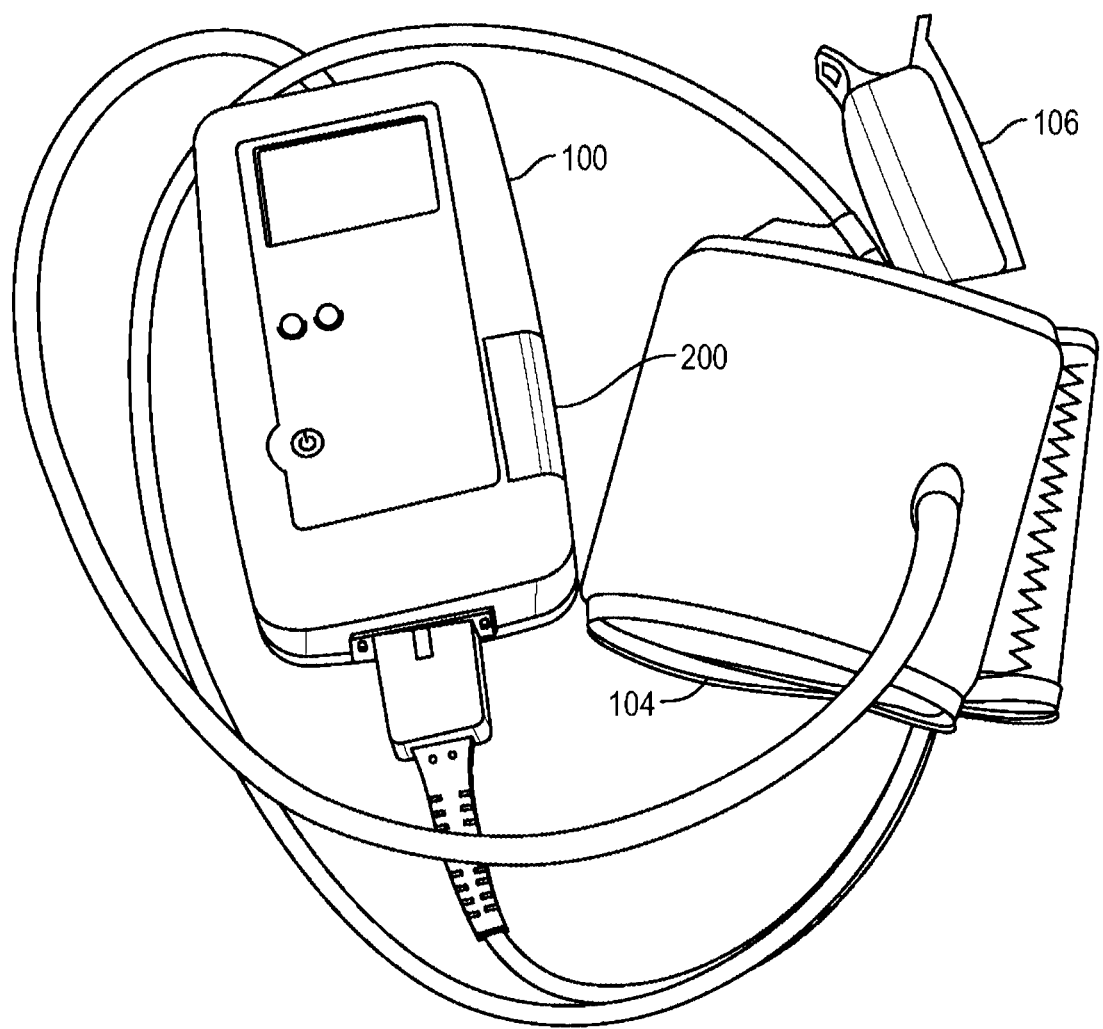
FIG. 2 shows the multi-parameter monitoring device operating in in a standalone mode, here drawing power from its internal battery.
Figure 3:
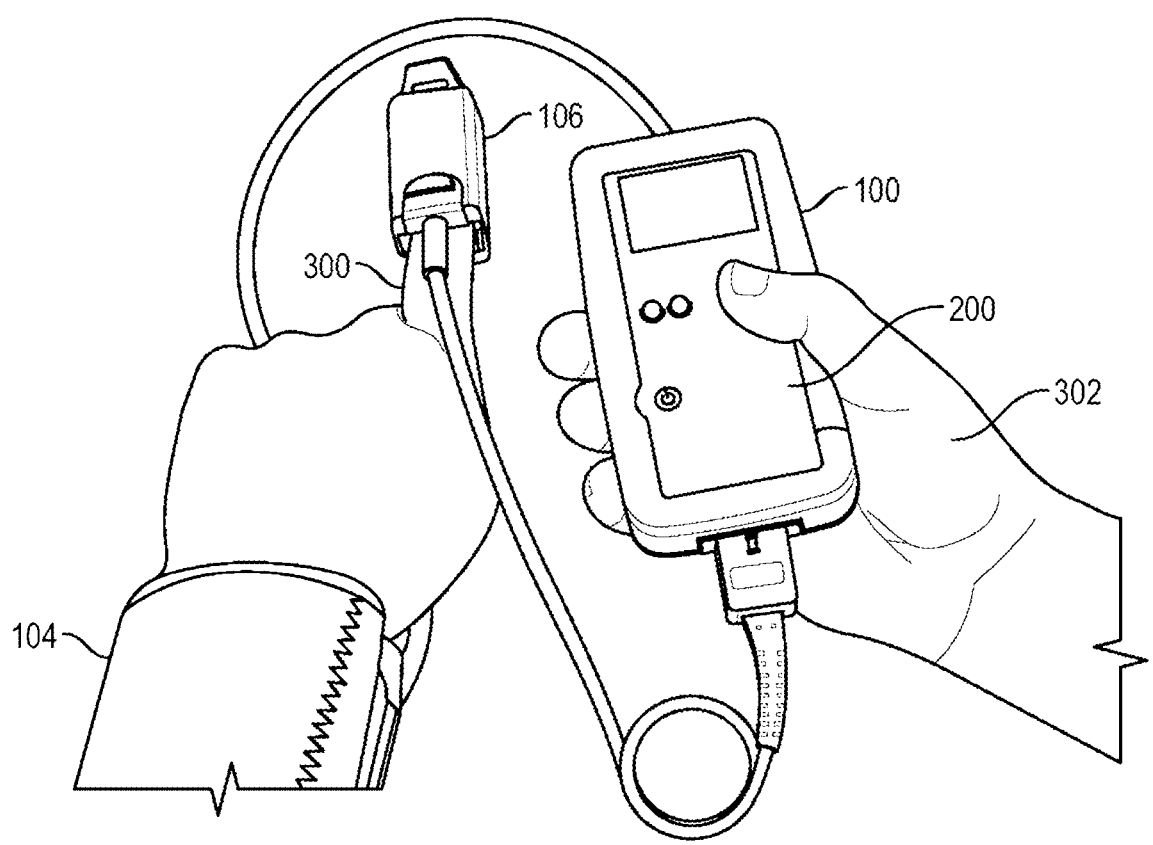
FIG. 3 shows an example of the multi-parameter monitoring device running a blood pressure measurement, ECG measurement, and blood oximeter measurement at same time.

The device can work either in external computer interface mode (e.g. PC mode) as shown in FIG. 1 or in a standalone mode running on batteries as shown in FIGS. 2 and 3.

FIG. 1 shows the multi-parameter monitoring device (100) operating in computer accessory mode, where the device may be controlled by another computerized device (102) through a data connection such as a USB or Bluetooth™ connection (here via a USB cable, and in FIG. 13 via a wireless Bluetooth™ connection), and in some embodiments also obtain power through the other computerized device (102). The device's blood pressure monitoring cuff (104) and finger mounted combination oximeter-ECG electrode (106) are also shown. In this embodiment, the device (100) may be powered though a USB cable connection (108) and exchange data with the other computerized device (102).

FIG. 1 shows two versions of the device: (100) shows the prototype device, while (100a) shows a possible industrial design for the commercial version of the device, along with the cuff (104a) and combination oximeter-ECG electrode (106a) for this more commercialized device.

FIG. 2 shows a close up of the multi-parameter monitoring device (100), pneumatic blood pressure cuff, first externally mounted ECG electrode (200) and finger mounted combination oximeter-ECG electrode (106). Here the device is not connected to an external computer, but rather is operating in in a standalone mode drawing power from its internal battery (see FIG. 7B).

FIG. 3 shows an example of the multi-parameter monitoring device (100) running a blood pressure measurement, ECG measurement, and blood oximeter measurement at same time in standalone mode.

In a preferred embodiment, the invention will be designed to be easy to use. For example, one first ECG electrode (200) may be integrated and onto the device box (e.g. external chassis) (100), and another other second ECG electrode may be integrated inside the finger mounted oximeter probe (106). Temperature sensors configured to monitor body temperature can optionally be mounted under either ECG electrode, or elsewhere as desired.

Here, for example, the finger mounted combination oximeter-ECG probe may be mounted on a digit (e.g. finger) of the patients (or users) left hand (300), while the patient (user) holds or touch the ECG pad with the right hand (302), thus allowing an ECG electrical connection that passes at least in part through the user's heart to be established.

Figure 4A:
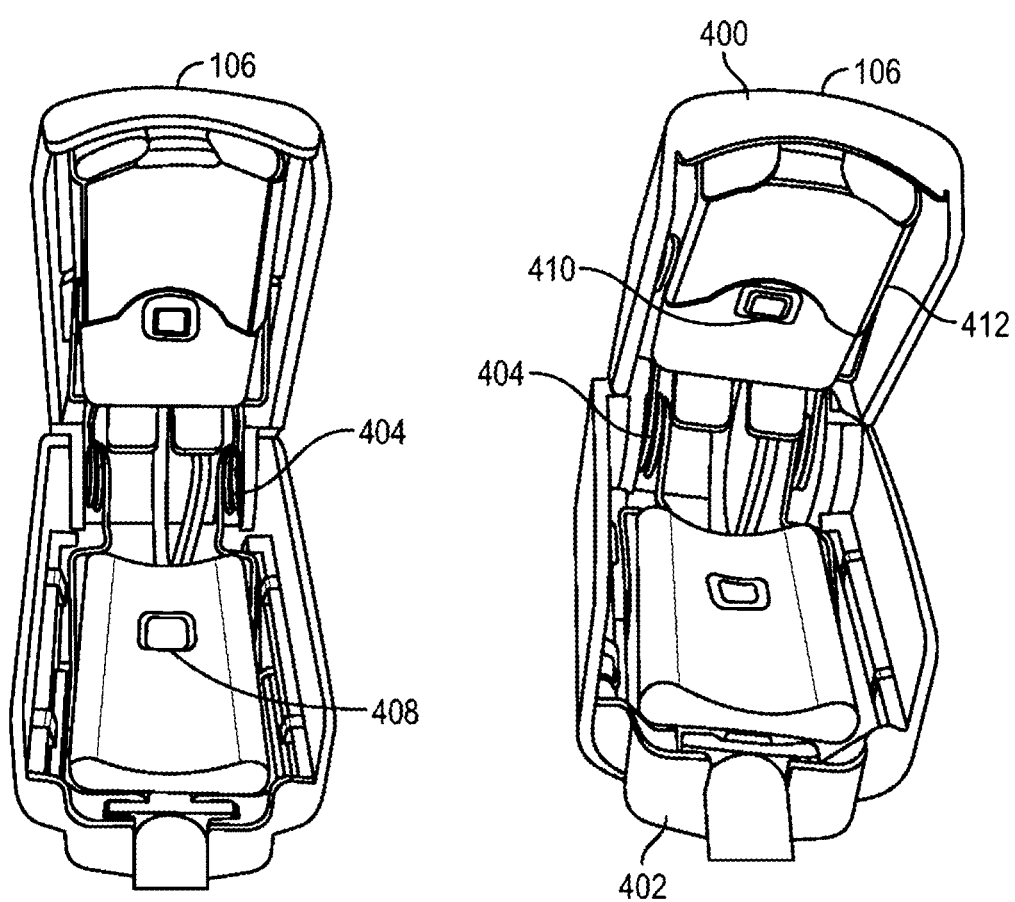
FIG. 4A shows the interior of the combination finger mounted oximeter and ECG electrode device, taken from two slightly different angles, showing the springs, finger baffle, oximeter LEDs and photodetectors, and the at least one ECG finger electrode.

The blood pressure, ECG and oximeter signals can be collected simultaneously. Each signal channel can work independently or in cooperation with other channels. The device software can recognize the configuration and process the data accordingly. Thus once the device is set up, minimal or no further operator intervention is needed. FIG. 4A shows the interior of the combination finger mounted oximeter and ECG electrode probe (106), taken from two slightly different angles, showing the probe's two clamshell sides (400), (402), springs (404), finger baffle (406), oximeter LEDs (408) and photodetectors (410), and the ECG finger electrode (412) (second ECG electrode).

Note that when discussing the combination finger mounted oximeter and ECG electrode, the frame of reference typically shifts to this combination finger mounted oximeter and ECG electrode. Just as a human mouth can open showing an interior of teeth, gums, and a tongue, and can then close again hiding these interior structures, so too this combination finger mounted oximeter and ECG electrode can also open and close. It is shown in "open" form in both FIG. 4A and FIG. 4B, and in closed form (closed around a finger of the user) in FIG. 3 (106). Thus, for example, the second ECG electrode (412) is considered to be on the interior of the combination finger mounted oximeter and ECG electrode probe (106).

Figure 4B:
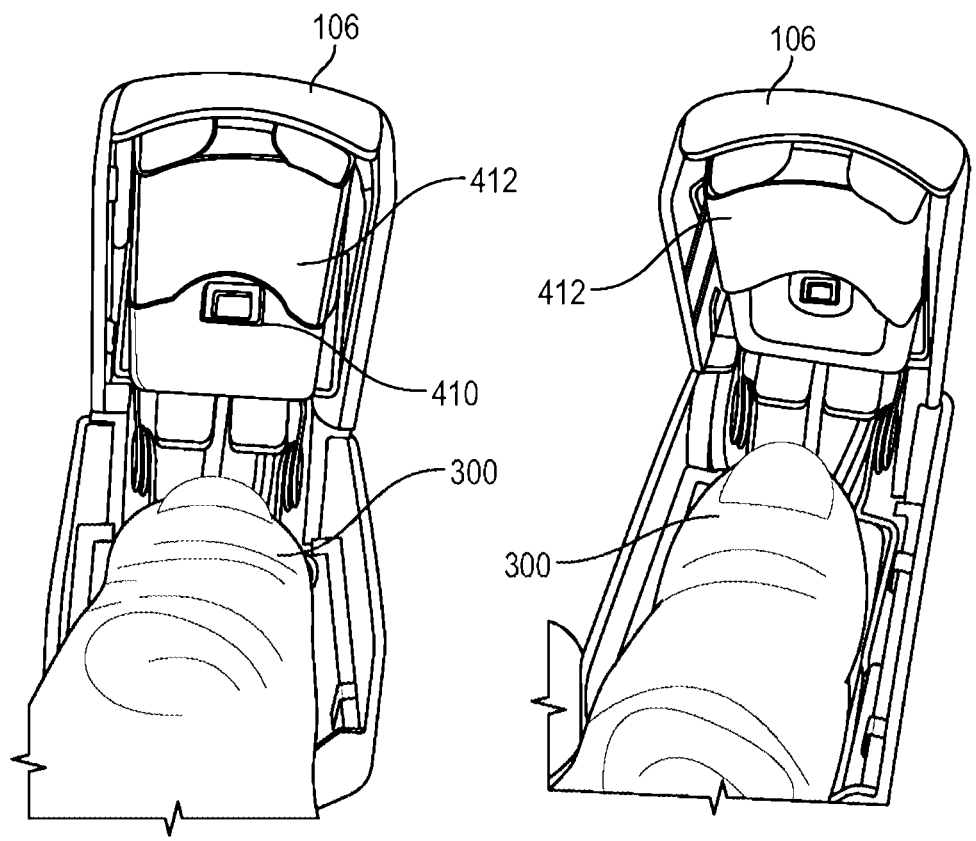
FIG. 4B shows how the user's finger interacts with the interior of the combination finger mounted oximeter and ECG electrode device. Here, to better see the oximeter optical sensors and the at least one ECG finger electrode, the two sides of the clamshell type finger probe are shown in an open configuration, but in use the two sides will be closed, thus bringing the oximeter sensor and the at least one ECG electrode in contact with the user's finger.

FIG. 4B shows how the user's finger (300) interacts with the interior of the finger mounted combination oximeter and ECG electrode device (106). Here, to better see the oximeter optical sensors and the ECG finger electrode, the two sides of the clamshell type finger probe are shown in an open configuration, but in use the two sides will be closed, thus bringing the oximeter sensor (410) and the second ECG electrode (412) in contact with the user's finger (300). A temperature sensor may optionally be mounted near 408 and/or 410 (not shown) or elsewhere.

Figure 5:
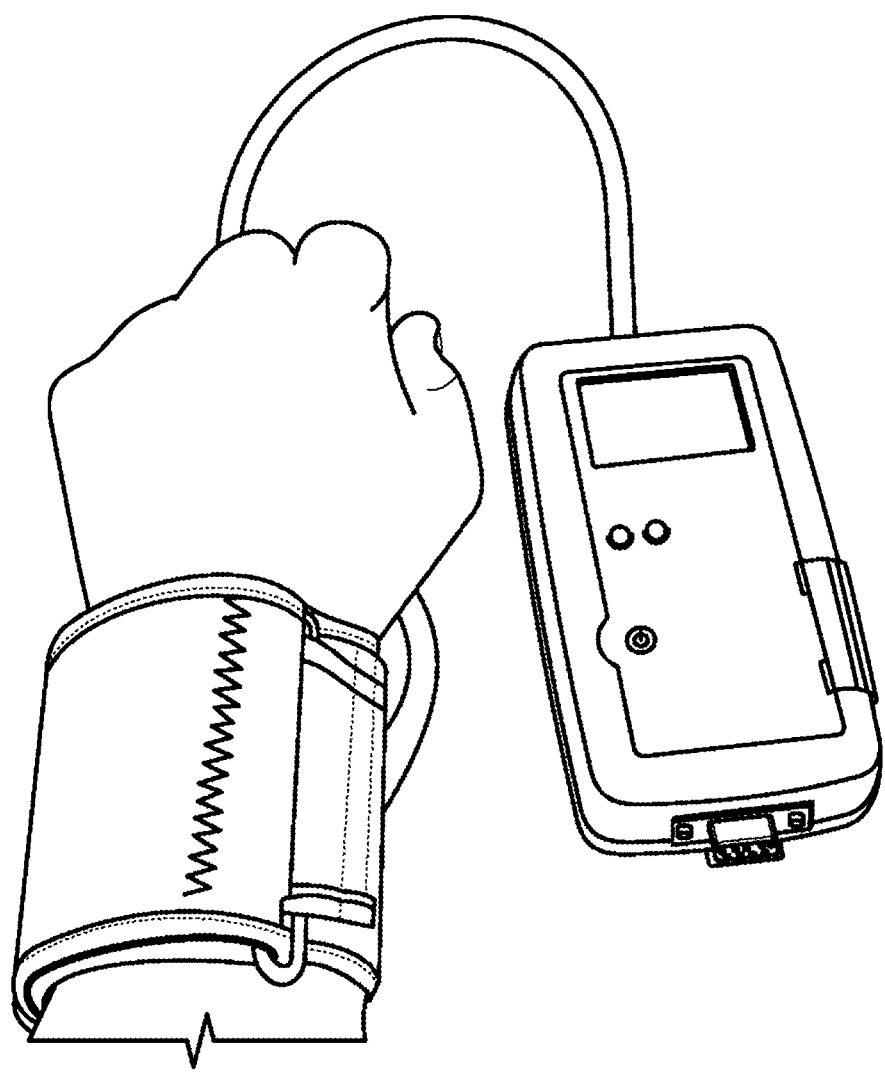
FIG. 5 shows the multi-parameter monitoring device working as a simple blood pressure monitor.

FIG. 5 shows that in some modes, the multi-parameter monitoring device can also operate as a simple, stand alone, blood pressure monitor.

Figure 6:
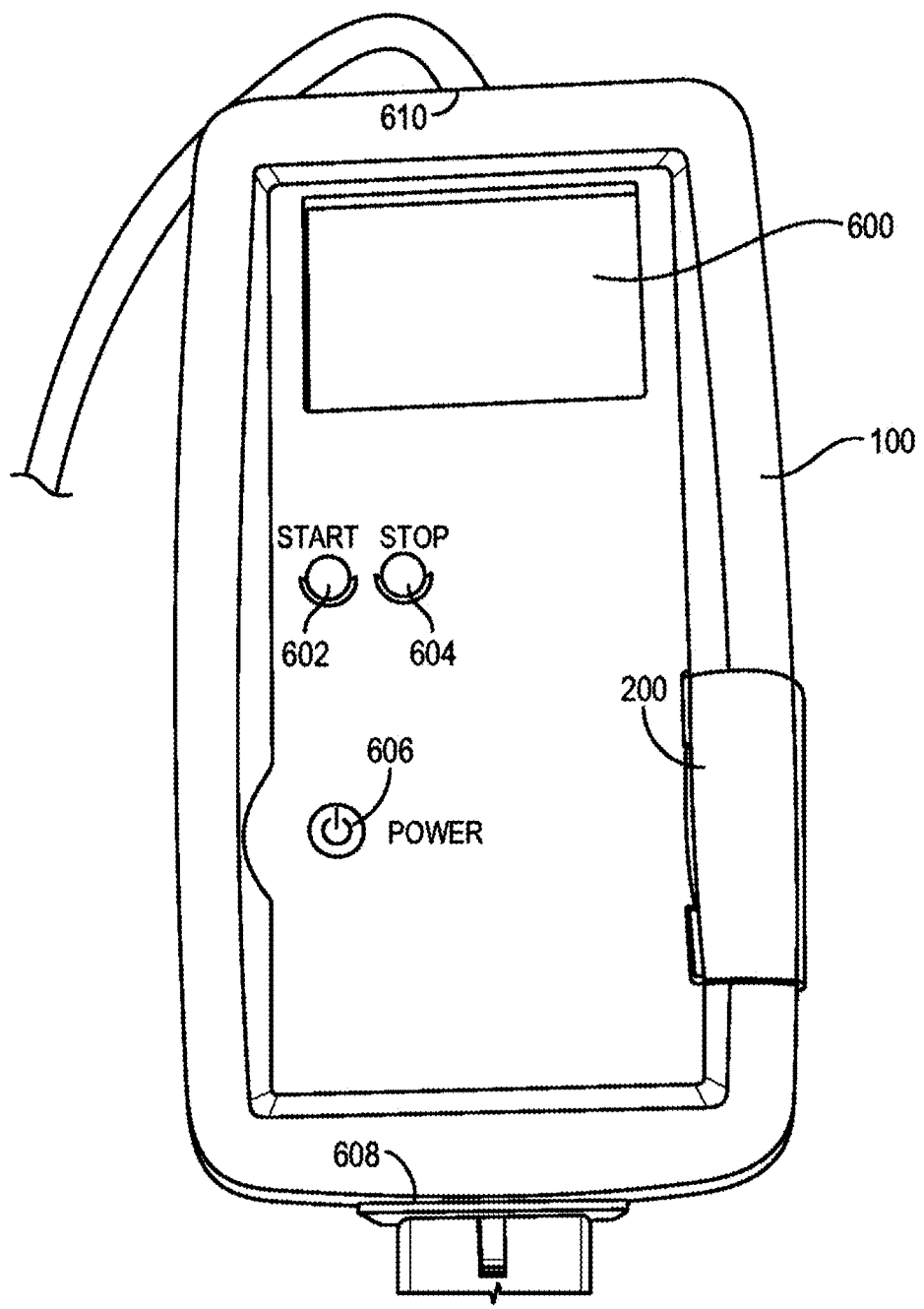
FIG. 6 shows the front panel of the multi-parameter monitoring device.

FIG. 6 shows a close-up of the front panel of the multi-parameter monitoring device (100), showing the device's optional built-in display (600), control buttons (602), (604), power button (606) and ports (608), (610). The device is also showing some patient readings directly on its optional built-in display (600).

In these discussions, unless otherwise stated, the frame of reference is usually the base unit chassis (100). This chassis has an exterior chassis cover (external chassis), and an interior. FIG. 6 shows the external chassis cover (100), which has an external chassis cuff port (610), a chassis mounted first ECG electrode (200), and an optional chassis mounted ECG-oximeter port (608). Optional external chassis mounted control buttons (602, 604), an optional external chassis mounted power button (606), and an optional external chassis mounted display screen (600) are also shown.

The device is designed to be simple to operate, and thus compatible for use by unskilled users in a home environment. For example, in some embodiments as shown in FIG. 6, using only the power button (606) and two control buttons (602), (604); the user can easily start/stop tests, as well as review test records that have been saved in the device's built-in flash memory. This particular embodiment system has a built in real-time clock/calendar, and generally all test records are time-stamped. This onboard Calendar/Timer may further have power backup, such as a built-in super capacitor, to allow time-keeping to continue even when the device is unpowered.

When run in standalone mode under battery operation, this particular embodiment (i.e. this particular device) uses a 160×100 greyscale graphic LCD (600) to display the various test operating instructions, modes and results. For example, optional built-in display (600) can show, ECG, finger pulse and cuff pressure pulse waveform data, along with date/time display, temperature display, blood pressure measurement display, heart rate, heart rate variation, systolic and diastolic pressure, and the like. This optional built-in display, or a different (e.g. external to the chassis) LCD display can also be used to review test record files, which contain the saved test records which cover blood pressure, temperature heart rate. As previously discussed, all test records may be time-stamped. Users can thus browse the test record based on testing date and time.

In a preferred or at least alternative embodiment, however, the device may be configured to communicate via a short range wireless connection, such as a Bluetooth® connection, to a local computerized device such as a smartphone or tablet computer. This local computerized device will typically be equipped with a high resolution color touchscreen, which will facilitate data display and analysis. This preferred or alternative "Bluetooth to smartphone" embodiment in action is shown in more detail in FIG. 13.

The start and stop buttons (602) and (604) can be used to start or stop the various measurements. In some embodiments, these start/stop buttons are multi-functional. When not in testing mode these two buttons can also be used for browsing the unit's on-chip test record file. Alternative control methods, such as using a built-in or remote touch sensitive display (600), can also be used.

Figure 7A:
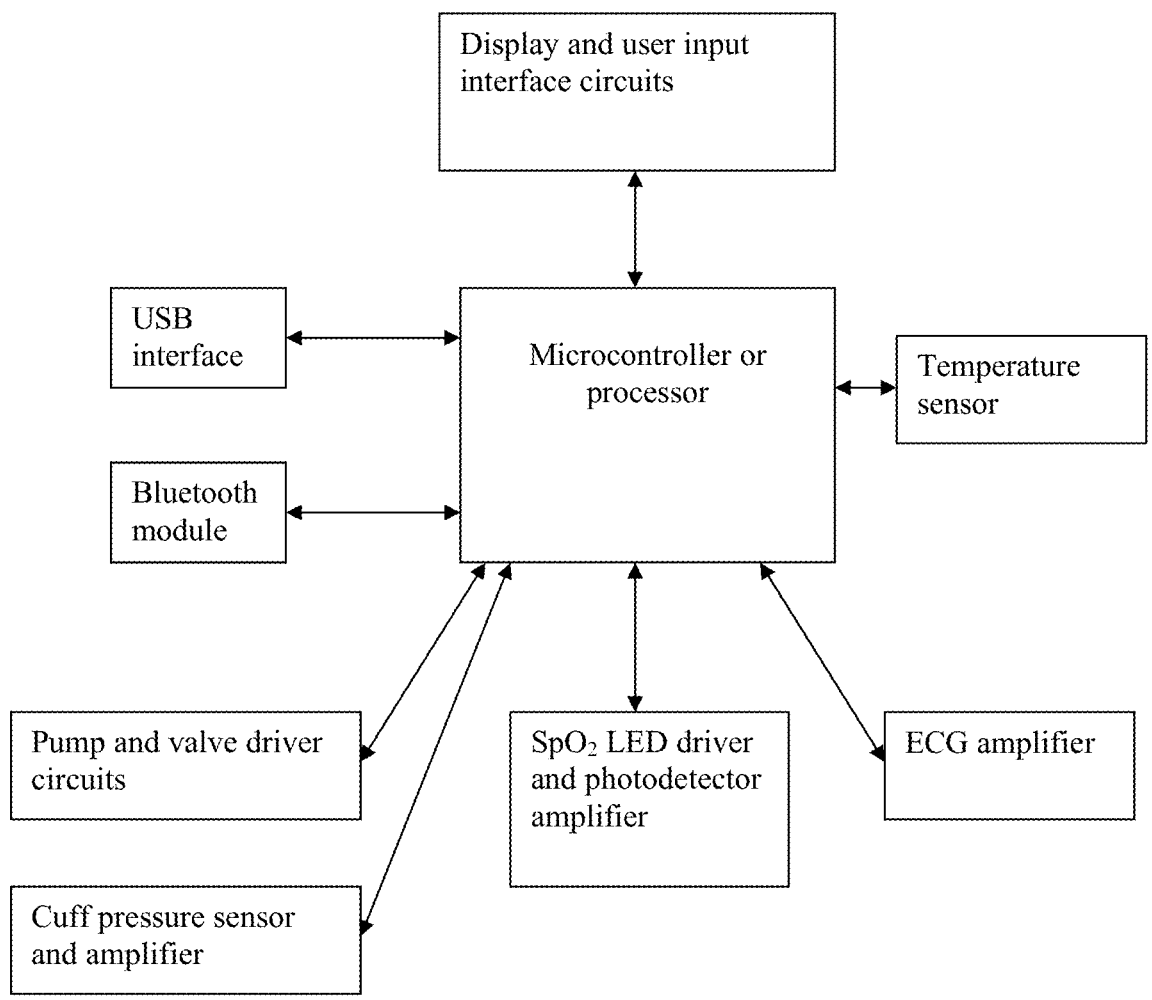
FIG. 7A shows a simplified electrical schematic of the multi-parameter monitoring device.

An overview of the device's various major electrical components is shown in FIG. 7A.

Figure 7B:
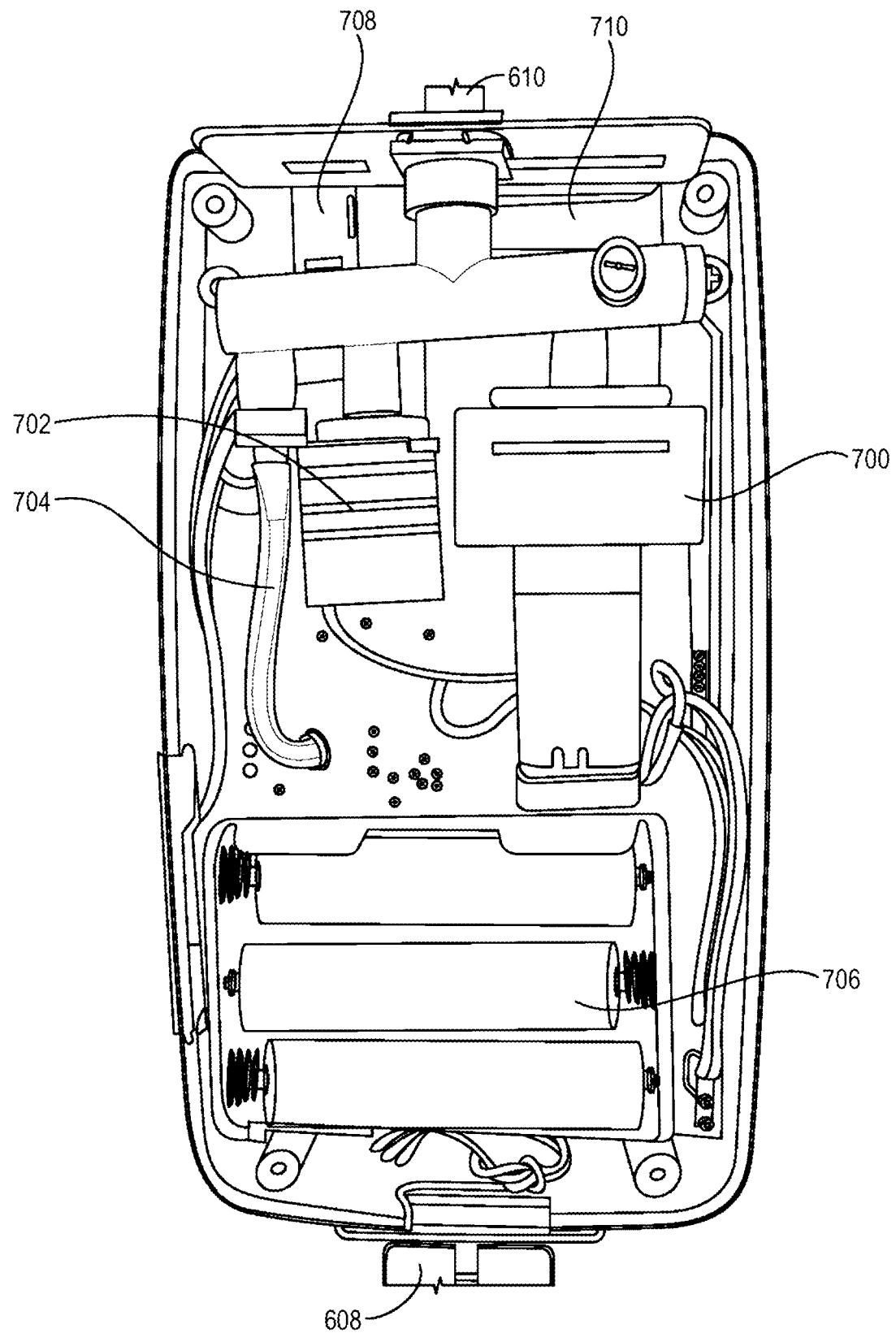
FIG. 7B shows a portion of the interior of the device, showing the device's pneumatic pump, valve, and tube connection to a microphone or pressure sensor, internal batteries, cuff port, port for the combination oximeter-ECG, USB port. A portion of the device's optional external memory SD card slot is also visible. In some embodiments, the interior of the device may also contain an interface for an optional temperature sensor. The temperature sensor or sensors may be mounted either on the device itself (often underneath the device's at least one ECG electrode) or on the clamshell type finger probe.

FIG. 7B shows a portion of the interior of the device, showing the device's pneumatic pump (700), valve (702), and hollow tube connection to a microphone sensor or pressure sensor (704), internal batteries (706), cuff port (610), port for the finger mounted combination oximeter-ECG probe, and mini-USB port (708). A portion of the device's optional external memory SD card slot (710) is also visible.

This particular device is capable of running under internal power using 3 AAA batteries (706), but can also draw power (5V/500 mA) from its USB interface if the device is connected to a suitable USB power source.

As previously discussed, the device may be designed with various flexible communication ports and interfaces. In one embodiment, the device can communicate with an external computerized device (e.g. a PC) (102) through the device's Universal Serial Bus (USB) port (708) or wireless Bluetooth™ transceiver. This particular device, as shown in FIGS. 1-7 features a USB interface (708) capable of full speed operation up to 12 M Byes/Sec, a Bluetooth 2.0 transceiver, and an SD memory card interface (710). This SD memory card interface allows large amount of data (e.g. 2 Gigabytes) to be logged and transferred to an external computerized device at any time, and thus serves as a useful supplement to the unit's standard internal flash memory.

Built-in Storage: In this particular example, the unit's on-chip file management system allows the user to save up to 1000 test records, which as described elsewhere generally cover blood pressure, temperature, heart rate, and heart rate variation. Each test record may be identified by a time stamp. The user can review these past test results directly on the device in standalone mode according to the date and time the testing was done. The data files are non-volatile, and the data can be retained even when device is powered off.

In addition to the various data acquisition channels previously discussed, the device may optionally also monitor the patient's temperature or ambient temperature and other parameters.

As previously discussed, the various data provided by this embodiment of the invention can also be analyzed by external software running on various external computerized devices, here exemplified by Windows based Personal Computers (PCs), (see FIG. 1, 102) but which can be any type of external device (e.g. smartphones, tablet computers, desktop computers, and the like), including remote servers.

In the FIG. 1 (102) example, and in the screenshots shown in FIGS. 8-11, this external analysis software is Microsoft Windows based software, capable of running under one or more processors (e.g. microprocessors) under various 32 and 64 bit windows operating systems including Windows XP, Windows Vista, Windows 7, 64 bit systems: Windows XP x64 Bit, Windows Vista x64 Bit, and Windows 7×64 Bit, Windows 8, and the like. In other embodiments, the external device analysis software may run under other operating systems such as iOS, Android, Linux, Unix, Windows and the like.

In some embodiments, internal or external device control and management software may include a data acquisition control graphical user interface (GUI). This GUI may do various functions such as real time waveform display for ECG, finger pulse determination, cuff pressure control and cuff pressure pulse determination.

Other functions may include real time temperature display, and/or provide a GUI for blood pressure measurement, waveform display for the ECG results, finger pulse results, cuff pressure results, as well as cuff pressure pulse during the deflation time of a blood pressure reading.

Various start/pause/stop buttons to may be used to control the cuff inflation and deflation process. Other GUI controls, such as various Zoom in/Zoom Out/Cursor buttons can be used to allow the user to easily view and analyze the various waveforms. Thus, for example, the user may pick one or more waveform peaks, calculate various waveform peak parameters, such as distance between peaks, and so on.

In some embodiments, an analyze button will allow the user to start various software analysis functions which can estimate heart rate, heart rate variation, systolic pressure, diastolic pressure and the like from either real-time data or from previously saved data.

Other GUI functions, such as patient information, can allow the user to input various patient related information into the system, such as patient age, gender, height, weight and so on.

Various Save/Read file buttons can be used to allow the user to save and retrieve various types of test raw data and other test related information.

Alternatively in some embodiments, the device may be connected to a local Bluetooth™ computerized device such as a smartphone (See FIG. 13, 1300), in which case the invention may be at least to some extent remotely controlled using the smartphone or other local computerized device. In such embodiments, the device itself may have no display, and be controlled partially or entirely using the computerized device's GUI display.

In some embodiments, the device software may also provide a GUI for various types of device built-in storage management. These functions can include functions such as download test records from the device, save test records to an external device file such as a PC file. Other functions may include buttons to allow the user to save device test record data to various file formats such as spreadsheet (e.g. Microsoft Excel) files. A read test records from PC file button/function can allow the user to retrieve various saved test records and view each test record as desired.

The external device software can also include a GUI for device configuration. This can be used, for example, to allow the user to read or set the device's clock/calendar timer, and/or allow the user to synchronize the device's time with the external computerized devices (e.g. PC) time. Other functions include allowing the user to choose various communication channel output modes (e.g. USB or Bluetooth) and allow a user check on the status of the device's built-in disk (e.g. solid state memory) capacity.

Figure 8:
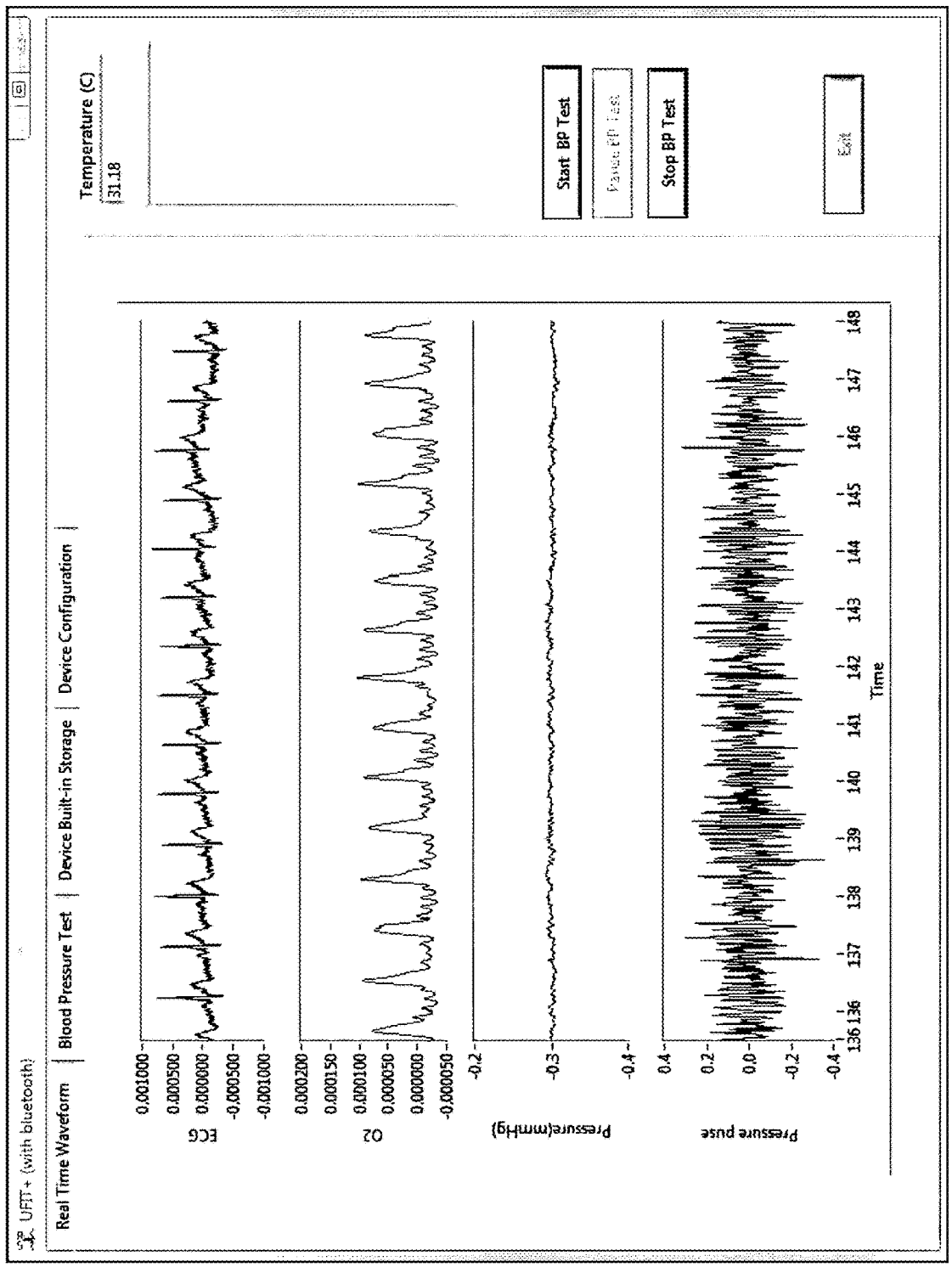
FIG. 8 shows how the external software portion of the invention, here running on an external computerized device, can receive the multi-parameter monitoring device's data, and display multiple channels of information on a graphical user interface (GUI). There real-time waveform displays of the pressure pulse, blood pressure, oximeter $O_2$ levels, and ECG waveforms are being displayed.

FIG. 8 shows how the external software portion of the invention, here running on an external computerized device (e.g. laptop, smartphone, tablet computer, and the like) can receive the multi-parameter monitoring device's data, and display multiple channels of information on a graphical user interface (GUI). There real-time waveform displays of the pressure pulse, blood pressure, oximeter $O_2$ levels, and ECG waveforms are being displayed.

Figure 9A:
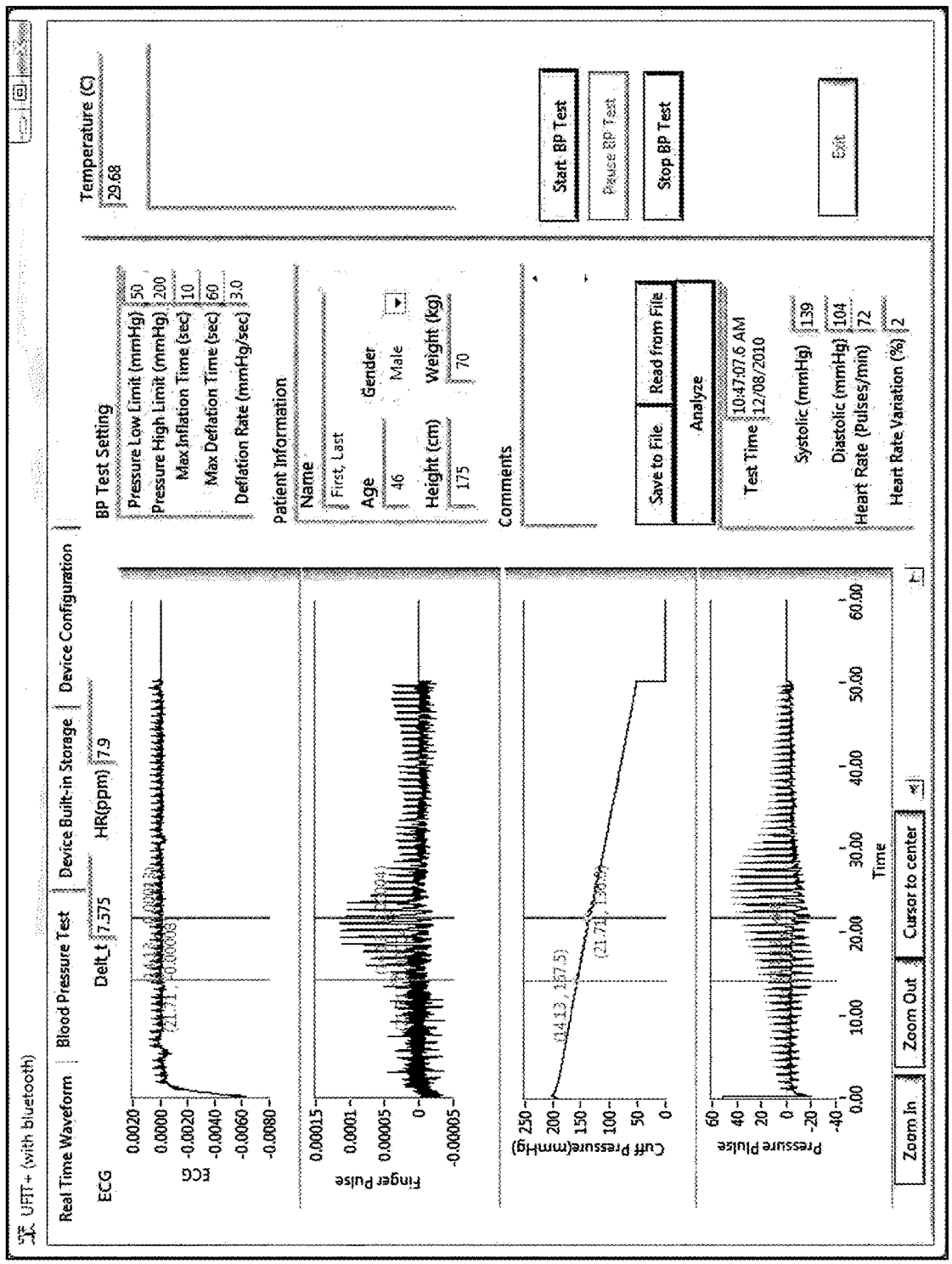
FIG. 9A shows how the external software portion of the invention, here running on an external computerized device can receive the multi-parameter monitoring device's data, and display on the external computerized device's screen, blood pressure measurements with additional ECG, finger pulse, and blood pressure. Additionally, various multi-parameter monitoring devices' testing settings, patient information, and data files can also be set or accessed through this GUI.

FIG. 9A shows how the external software portion of the invention, here running on an external computerized device can receive the multi-parameter monitoring device's data, and display on the external computerized device's screen, blood pressure measurements with additional ECG, finger pulse, and blood pressure. Additionally various multi-parameter monitoring devices' testing settings, patient information, and data files can also be set or accessed through this GUI.

Figure 9B:
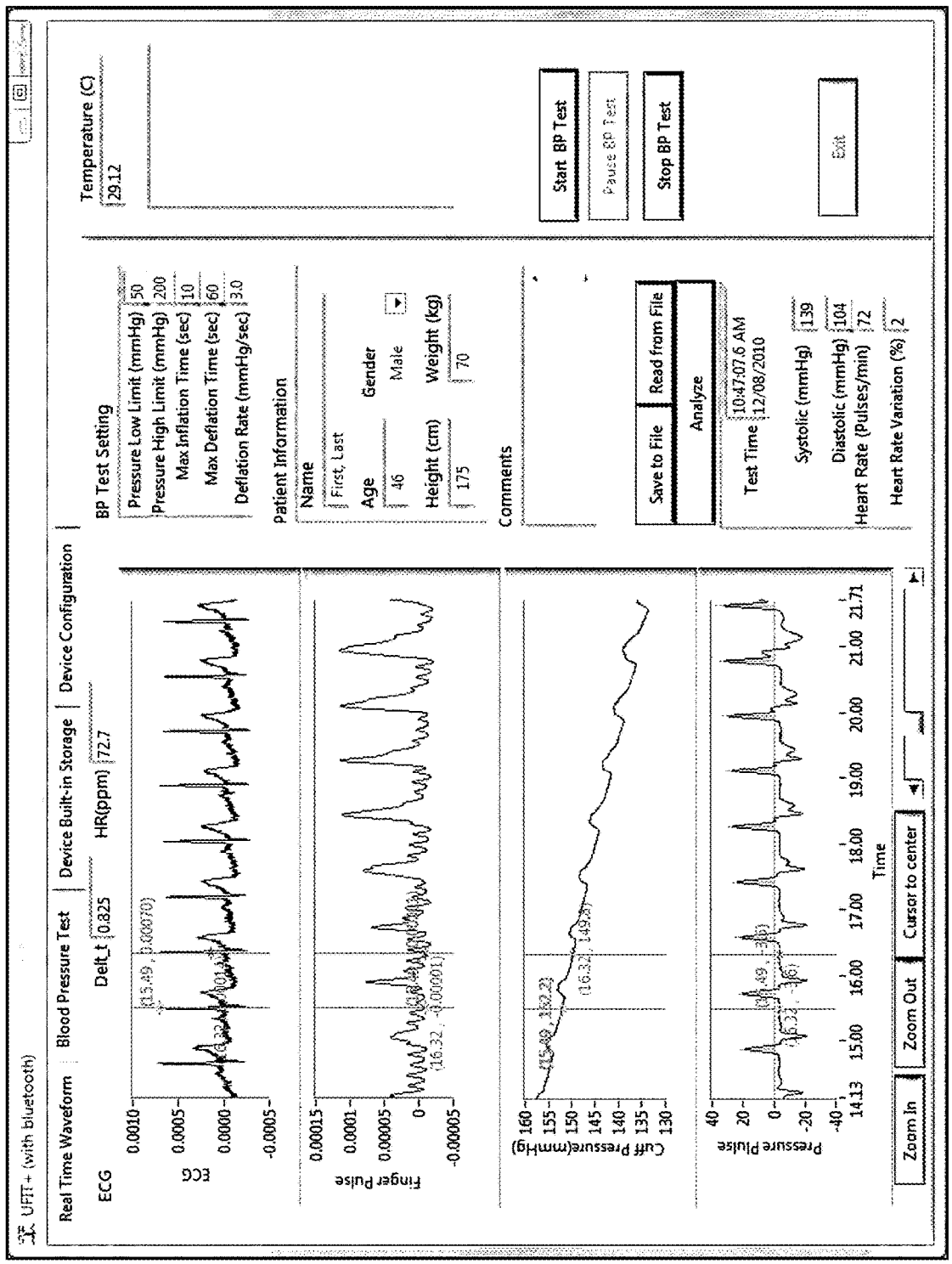
FIG. 9B shows how the user may zoom in to display more details of the various physiological waveforms previously shown in FIG. 9A.

FIG. 9B shows how the user may zoom in to display more details of the various physiological waveforms previously shown in FIG. 9A.

Figure 10:
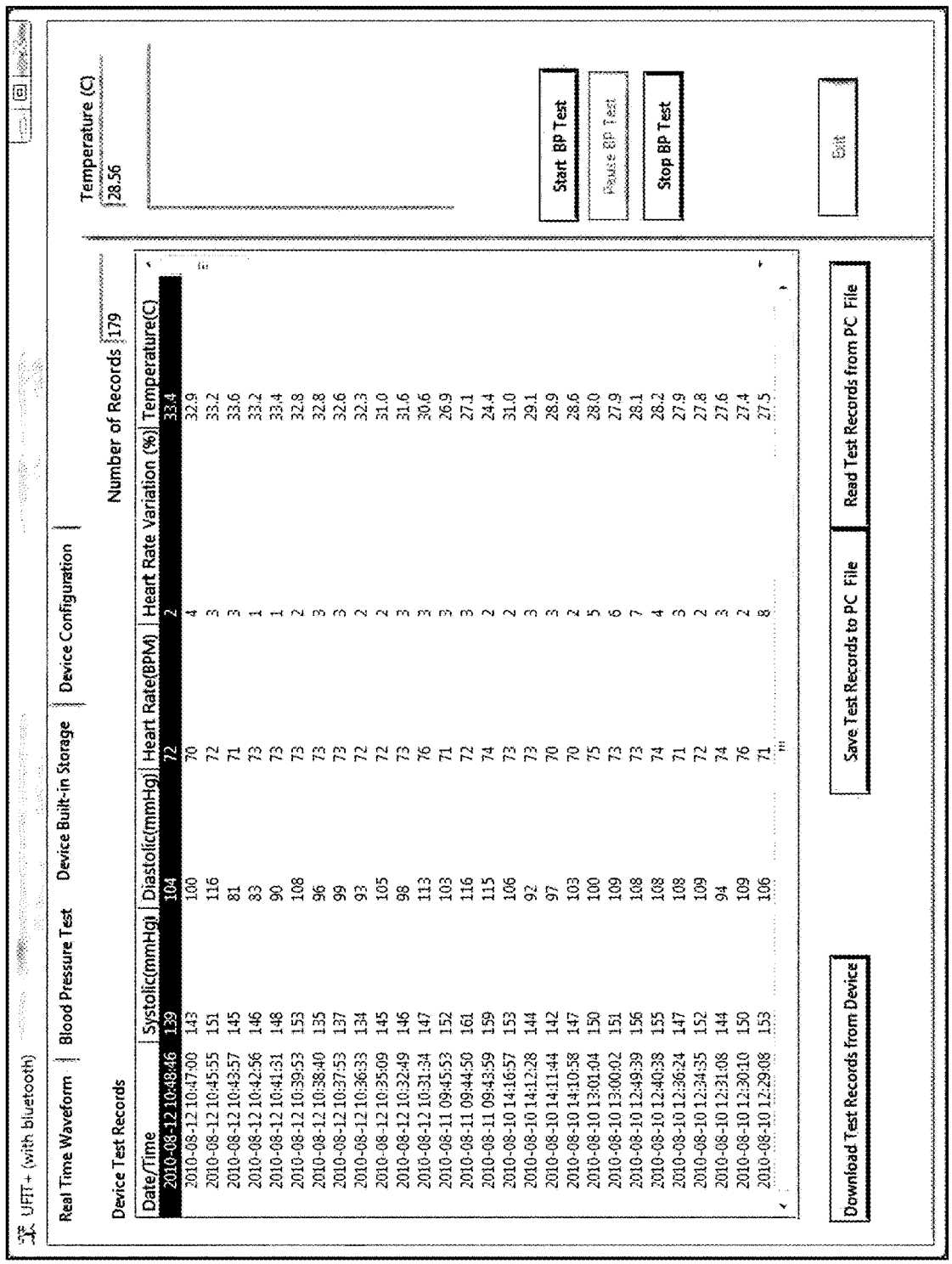
FIG. 10 shows how the external software portion of the invention, here running on an external computerized device, can also be used for managing the multi-parameter monitoring device's various files of test records
Figure 11:
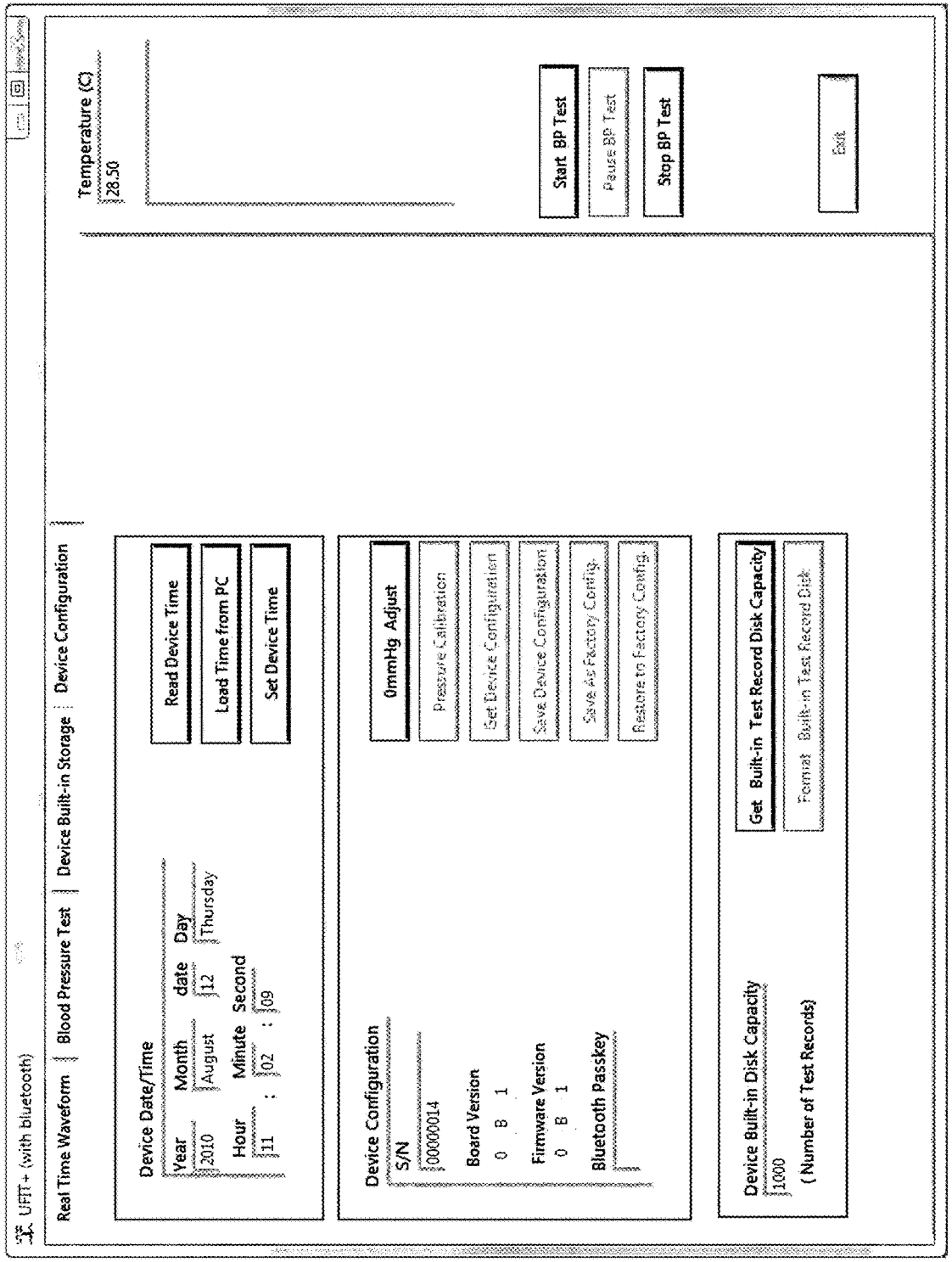
FIG. 11 shows how the external software portion of the invention, here running on an external computerized device, can also be used to manage the multi-parameter monitoring device's configuration settings and other functions, such as the multi-parameter monitoring device's real-time clock/calendar.

FIG. 10 shows how the external software portion of the invention, here running on an external computerized device, can also be used for managing the multi-parameter monitoring device's various files of test records FIG. 11 shows how the external software portion of the invention, here running on an external computerized device, can also be used to manage the multi-parameter monitoring device's configuration settings and other functions, such as the multi-parameter monitoring device's real-time clock/calendar.

Figure 12:
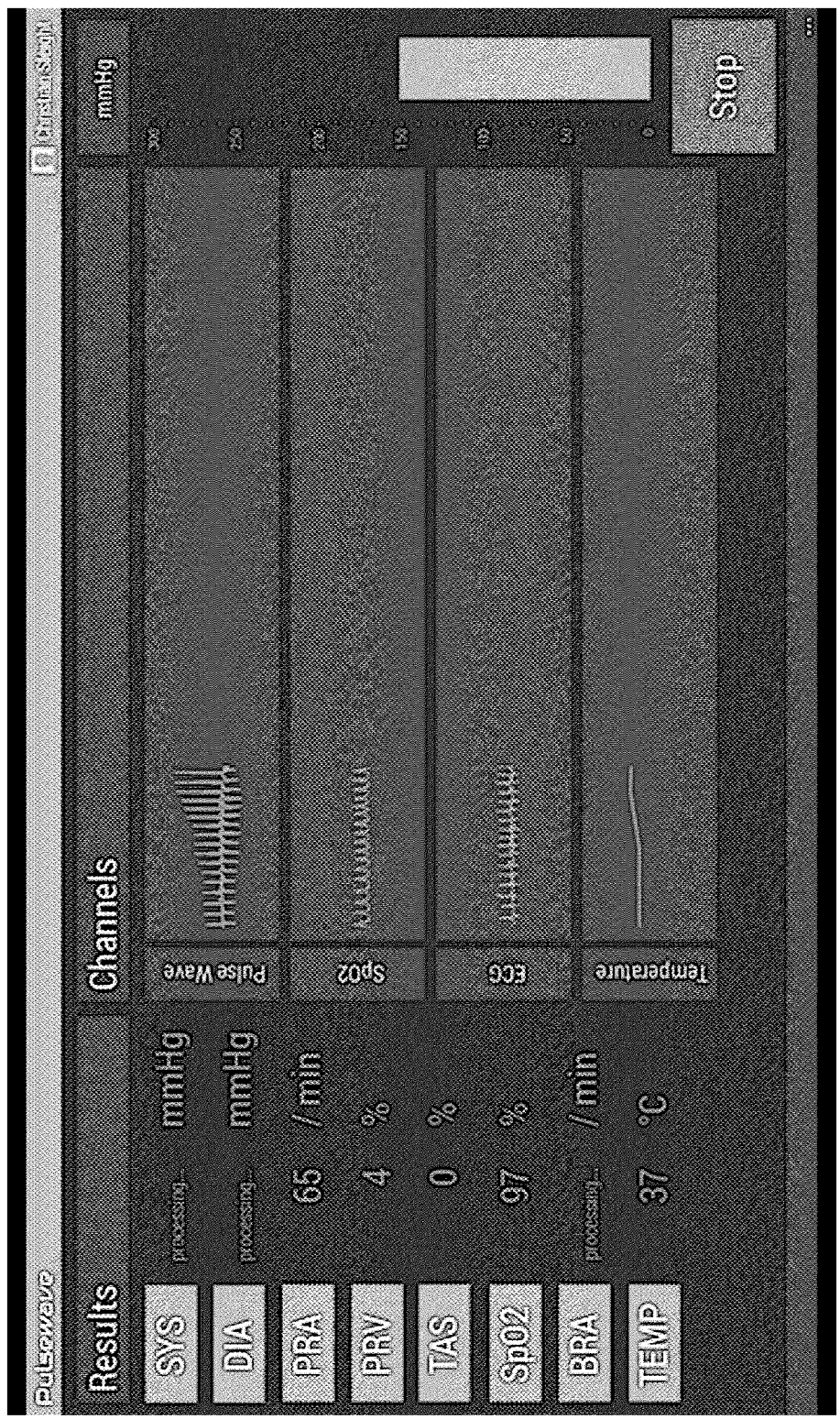
FIG. 12 shows an alternative software portion of the invention, here optimized to run on a tablet type external computerized device, using signals further processed by a remote server. This tablet display shows the output of various physiological parameters determined either directly from the device, or computed indirectly using various algorithms. The results include systolic blood pressure (SYS), diastolic blood pressure (DIA), pulse rate average (PRA), pulse rate variability (PRV), heart arrhythmia (TAS), blood oxygen saturation (SpO2), breathing rate average (BRA), and body temperature (TEMP).

FIG. 12 shows an alternative software portion of the invention, here optimized to run on a tablet type external computerized device, using signals further processed by a remote server, showing output of various physiological parameters including systolic blood pressure (SYS), diastolic blood pressure (DIA), pulse rate average (PRA), pulse rate variability (PRV), heart arrhythmia (TAS), blood oxygen saturation (SpO2), breathing rate average (BRA), and body temperature (TEMP).

Figure 13:
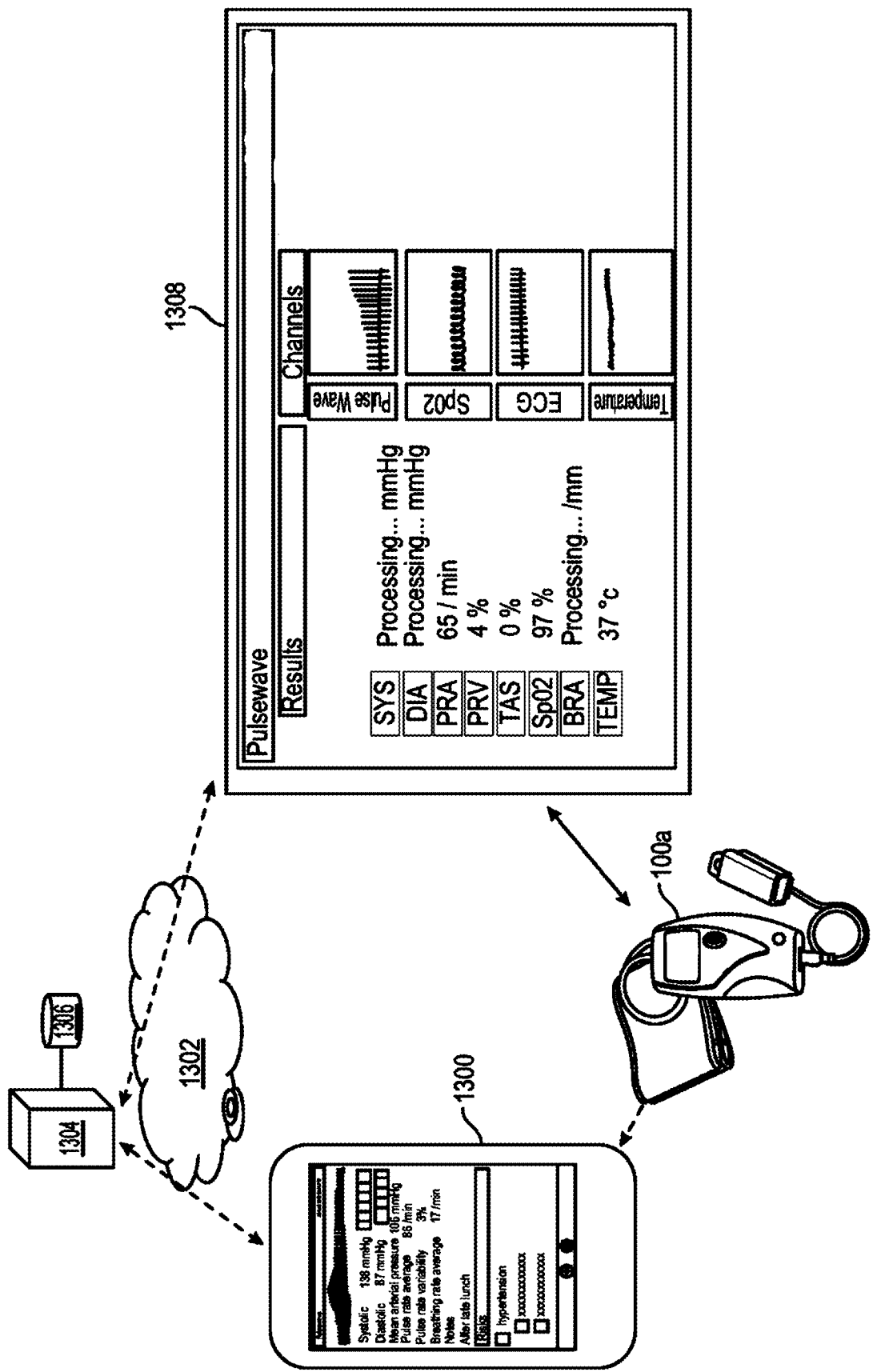
FIG. 13 shows an example of the device sending data via Bluetooth™ to a local Bluetooth equipped smartphone, and the smartphone in turn transmits (relays) this data to a remote internet server for further analysis. The patient or physician can then download this server analyzed data to their local computerized devices (here a tablet device) for subsequent evaluation, and/or configure the server to automatically react in certain situations.

FIG. 13 shows an example of the diagnostic device (100) sending data via a wireless Bluetooth® connection to a local (to the patient) Bluetooth equipped smartphone (1300). This smartphone in turn transmits data over the internet (1302) to a remote server (1304) and server memory (1306) for further analysis. At the server, the physician or other healthcare professional can analyze the data using either standardized algorithms, or alternatively using physician selected algorithms that are, at least some extent, customized to that particular patient, or customized according to physician preference. The patient or physician can then download this server analyzed data to their local computerized devices (here a tablet device 1308) for subsequent evaluation.

The server can comprise at least one processor (often chosen from the popular x86, ARM, or MIPS family of processors), Internet network interface, memory, an operating system (e.g. Linux, Unix, Windows), and various ancillary programs such as web server software (e.g. Apache), database management programs (e.g. MySQL, MariaDB, MongoDB, etc.), various scripting languages (e.g. Perl, Python, PHP and the like) as well as the various specific web pages, scripts, and other programs used to implement the functionality disclosed herein.

Although software and algorithms running on one or more processors aboard the local device (1300), the physician's remote device (1308) or even on the diagnostic device (100) itself can in principle perform many different types of analysis, there are a number of advantages to allowing the remote server (1304) and memory (1306) to take on at least some of the burden of data storage and data analysis. These are:

1: Due to the fact that the server memory (1306) has a potentially unlimited capacity, as well as due to the fact that it will be frequently updated with the results from a large number of different patients, the server algorithms can make use of various features, such as pattern recognition, that would not be as feasible on other devices.

2: Due to the fact that the server algorithms can be under physician control, this enables (with proper safeguards) the physician to customize the algorithms to the preferences of that particular physician and patient. For example, a physician may choose to go to a more sensitive setting, and accept the risk of more false alarms, from a known critically ill COPD patient. By contrast, the same physician, knowing that another patient is relatively healthy, may choose to select a less sensitive setting that generates fewer false alarms. Additionally, some physicians may wish to suppress alerts from all but the most urgent situations, while other physicians may wish to generally get more frequent alerts from their respective patients.

3: Due to the fact that the server can also have access to population data from a large number of patients, as well as population data from a large number of similarly designed devices, the server approach also can provide superior quality assurance (Q/A) and control. This is particularly useful in home monitoring situations, where Q/A concerns are often higher than in professional use situations. For example, the server software may be configured to perform additional checks to confirm that the data being collected is reasonable, as well as additional checks to detect potential errors during data acquisition. The server software may also be configured, as needed, to request the user to repeat collections as needed, set or change data collection intervals, recommend proper data collection settings, and the like.

Additionally, putting the algorithms on a server enables the physician to use more advanced analysis algorithms that may, for example, have been validated by various academic publication, and/or even officially recommended by the medical association for that particular disease, but which may not have yet been approved by the Food and Drug Administration for routine use in embedded medical devices. This can, depending upon physician judgment, actually improve patient safety and care because FDA review of new software algorithms intended to be embedded permanently into medical devices can be very slow and expensive. Indeed it can be so slow and expensive that many promising and clinically useful algorithms may never obtain official FDA approval for embedding into medical devices for general purpose use.

Although this patent application is not intended to provide legal or regulatory advice, historically the FDA has generally been more permissive about allowing physicians to use their minds and supplementary physician calculating tools, such as spreadsheets. The present invention's "Cloud Diagnostics™ " approach allows physicians to extend their minds and calculating tools to select various algorithms that may be most appropriate to their particular patients, without the enormous burden of having to prove that the algorithm works for all patents at all times. So long as the physician or the medical society is willing to assume risk and liability for their use, then a wider variety of useful algorithms may be used then would otherwise be possible. This can result in better patient care and superior outcomes.

As an example of this, consider the case of an American physician who realizes that his patients are being inadequately served by systems that are presently being marketed. Suppose that in response to a peer reviewed articles such as Jensen et. al., "*Clinical impact of home telemonitoring on patients with chronic obstructive pulmonary disease., Telemed J E Health,* 2012 November; 18(9) 674-8, a well-respected COPD medical society has recently recommended this approach as the proper standard of care for this disease. Suppose also that the physician is also unwilling to wait an unknown amount of time, likely many years if ever, until FDA approved devices implementing this recommended method are on the market, because most probably many of the physician's patients will die in the meantime.

To avoid these preventable deaths, the physician instead can use the invention to set up a semi-automated system that recommends changes in antibiotics and steroid administration (or other drugs) in response to patient uploaded measurements of systolic and diastolic blood pressure, pulse rate, and blood oxygen saturation. Here the physician may simply upload or otherwise select appropriate server analysis parameters, and have the system automatically inform the physician and patient when drug dosage changes may be advisable.

The patient can thus receive a nearly instant alert when medication should be adjusted. As a safety precaution, the server software can be set up to allow the physician to review and override these server generated recommendations if, in the physician's judgment, they are inappropriate. The remote server system can thus be set up so that the physician's professional judgment can remains in the loop at all times, but the system can provide extremely rapid (i.e. responses on the order of seconds) response times. Reliability can be improved as well, because the sever can respond 24 hours a day, seven days a week, and thus continue to apply the physician's best judgment even during periods when the physician may be asleep, distracted, or otherwise unavailable.

Thus in some embodiments, the invention may comprise a system or method of simultaneously monitoring pulse waveforms indicative of blood pressure, blood oxygen levels, and electrocardiogram signals. This method uses a portable handheld base unit comprising a base unit processor, software, memory, external chassis, and user control inputs. This handheld base unit will typically further comprise an air pump and valve mounted inside this external chassis. These are used to drive (usually via tubing) a blood pressure monitoring cuff. The base unit will typically have at least one detector to monitor pulse input from this blood pressure monitoring cuff, and often an external chassis mounted cuff port to accommodate this tubing.

The base unit will often further comprise a portion of an ECG device comprising two or more leads. This ECG device will typically comprise an external chassis mounted first ECG electrode configured to touch a patient's hand while the patient is holding the handheld base unit. The ECG device will typically also comprise an ECG amplifier and an external chassis mounted electrical ECG-oximeter port for receiving input from a second ECG electrode.

The invention also uses an external combination finger pulse oximeter-ECG electrode device that is configured external to this external chassis. This external combination finger pulse oximeter-ECG electrode device will typically comprise an interior with at least a second ECG electrode.

The device's processor is further configured to drive, often via the electrical ECG-oximeter port, a plurality of finger pulse oximeter light sources at a plurality of wavelengths, as well as to receive photodetector signals from the external combination finger pulse oximeter-ECG electrode device. The device's processor is typically also configured to drive the blood pressure monitoring cuff (which, in some embodiments, is connected to the external chassis mounted cuff port, but which in other embodiments, can be a stand-alone cuff connected to the device's processor using a wireless link).

The device's processor is typically also configured to drive the external combination finger pulse oximeter-ECG electrode device (which, in some embodiments, is connected to the external chassis mounted electrical ECG-oximeter port, but in other embodiments, can be a self-contained combination finger pulse oximeter-ECG electrode device connected to the device's processor using a wireless link).

In use, to obtain electrocardiogram pulse wave information, the blood pressure monitoring cuff will be placed around a limb of a patient, and the external combination finger pulse oximeter-ECG electrode device will be placed around the patient's finger (or toe or other digit).

The patient may also be instructed to hold the base unit so that the first ECG electrode makes electrical contact with the patient's hand (while the patient is holding the base unit), while at the same time, the second ECG electrode makes electrical contact with the patient's finger, toe, or other digit, preferably not on the same hand that is holding the base unit (e.g. on a different hand, or on a toe).

This system or method will thus produce synchronized pulse wave, hemoglobin absorbance, and ECG waveforms of the same patient heart beats by using the base unit processor, and the air pump and valve, to apply varying amounts of air pressure to the cuff and obtain pulse wave information data from this cuff as a function of air pressure. At the same time, the system or method's base unit will simultaneously drive the external combination finger pulse oximeter-ECG electrode device at a plurality of wavelengths, and use the base unit processor and the photodetector to obtain blood hemoglobin absorbance information data as a function of wavelength and as a function of the patient's pulse wave.

Thus the system or method will use the base unit to simultaneously monitor electrical signals from at least the first ECG electrode and the second ECG electrodes, and additionally use the base unit processor to do at last one of a) mathematically processing and storing, and/or b) directly storing, versions of:

blood pressure monitoring pulse wave information
external combination finger pulse oximeter-ECG electrode device blood hemoglobin absorbance information as a function of wavelength and pulse wave
and said electrocardiogram pulse wave information
in either local memory or remote memory.

In some embodiments, the present invention may also be used for drug monitoring purposes. Here the entire disclosures of parent application Ser. Nos. 15/954,250 and 15/060,514 are incorporated herein by reference. Thus in some embodiments, the device software itself may be used for drug monitoring as per Ser. Nos. 15/954,250 and 15/060,514 without the need of using external servers. Alternatively, in some embodiments, the device software may work in conjunction with remote server software, as per Ser. Nos. 15/954,250 and 15/060,514, for drug monitoring purposes.

Trademarks: Bluetooth® is both a trademark of the Bluetooth special interest group, as well as a common term to refer to the IEEE 802.15 set of standards for wireless connectivity. Cloud Diagnostics™ is a trademark of Cloud Dx, Inc.

The invention claimed is:

1. A portable handheld device for simultaneously monitoring pulse waveforms indicative of blood pressure, blood oxygen levels, and electrocardiogram signals of a patient, said device comprising:
   an ECG device comprising at least two leads;
   a handheld base unit comprising a base unit processor, software, memory, external chassis, and user control inputs;
   said handheld base unit further comprising an air pump and valve, mounted inside said external chassis, for driving a blood pressure monitoring cuff comprising tubing, at least one detector to monitor pulse input from said blood pressure monitoring cuff, and an external chassis mounted cuff port to accommodate said tubing for said blood pressure monitoring cuff;
   said blood pressure monitoring cuff configured to be placed around a limb of a patient;
   said handheld base unit further comprising a portion of said ECG device, said ECG device further comprising:
   a) an external chassis mounted first ECG electrode configured to touch said patient's hand while said patient is holding said handheld base unit;
   b) an ECG amplifier;
   c) an external chassis mounted electrical ECG-oximeter port for receiving input from a second ECG electrode;
   d) an external combination finger pulse oximeter-ECG electrode device configured external to said external chassis and configured to be placed around a digit of said patient;
   e) said external combination finger pulse oximeter-ECG electrode device comprising an interior, said interior comprising a second ECG electrode;
   said processor further configured to apply, over a plurality of patient heart beats, varying amounts of air pressure to a blood pressure monitoring cuff connected to said external chassis mounted cuff port and obtain pulse wave information from said cuff;
   said processor and said electrical ECG-oximeter port further configured to simultaneously drive, over a plurality of patient heart beats, a plurality of finger pulse oximeter light sources at a plurality of wavelengths, and to receive photodetector signals from said external combination finger pulse oximeter-ECG electrode device;
   said processor and said device also configured to simultaneously drive said external combination finger pulse oximeter-ECG electrode device at a plurality of wavelengths, and obtain blood hemoglobin absorbance information as a function of wavelength and as a function of pulse wave;
   said processor and said device further configured to simultaneously monitor, over said plurality of patient heart beats, electrical signals from said first ECG electrode and second ECG electrodes to obtain synchronized pulse wave, hemoglobin absorbance, and electrocardiogram pulse wave information of a same said plurality of patient heart beats;
   wherein said processor is configured to direct said base unit processor to implement at least one of:
   i) mathematically processing versions of simultaneously obtained blood pressure monitoring pulse wave information, external combination finger pulse oximeter-ECG electrode device blood hemoglobin absorbance information as a function of wavelength, said pulse wave information, and said electrocardiogram pulse wave information, and store in local or remote memory; and
   ii) directly storing direct versions of simultaneously obtained blood pressure monitoring pulse wave information, external combination finger pulse oximeter-ECG electrode device blood hemoglobin absorbance information as a function of wavelength, said pulse wave information, and said electrocardiogram pulse wave information in said local or remote memory.

2. The device of claim 1, wherein said software and base unit processor is further configured to use said blood hemoglobin absorbance information as a function of wavelength and as a function of pulse wave to further correct an accuracy of blood pressure monitoring information obtained from said blood pressure monitoring cuff.

3. The device of claim 1, wherein said device is configured to transmit any or all of blood pressure monitoring pulse wave information data, external finger pulse oximeter-ECG electrode device blood hemoglobin absorbance information data, and said electrocardiogram pulse wave information, along with device air pressure information data and light source driving information data, to an external computerized device or remote server via a wired, wireless, or optical communications port.

4. The device of claim 3, wherein said external computerized device or remote server is configured to mathematically analyze said data and produce any of mathematically computed blood pressure, blood oxygen level, ECG results, graphs of said data, and report on said mathematically computed blood pressure, blood oxygen level, and ECG results.

5. The device of claim 3, wherein said external computerized device is a remote server, and wherein said remote server is further configured to analyze said data according to patient specific algorithms customized for a health status of an individual patient using said device; and
   wherein said remote server is further configured to automatically generate at least one of medical alerts or drug dosage advisory messages according to patient specific algorithms customized for said health status of said individual patient; or
   wherein said remote server is further configured to automatically generate quality assurance alerts.

6. The device of claim 1, wherein at least one of said plurality of light sources is set at a wavelength where an absorbance of blood hemoglobin changes substantially as a function of a degree of oxygenation of said blood hemoglobin, and at least one of said plurality of light sources is set at a wavelength where said absorbance of blood hemoglobin changes minimally as a function of said degree of oxygenation of said blood hemoglobin;

and where said air pump and valves are configured to deliver air pressure to said cuff at varying pressure levels set to allow said device to obtain blood pressure readings.

7. The device of claim 1, further comprising a blood pressure monitoring cuff configured to detachably plug into said external chassis mounted cuff port; and any of:
   a) a combination external pulse oximeter-ECG electrode device configured to detachably plug into said electrical ECG-oximeter port; and
   b) a combination external pulse oximeter-ECG electrode device configured to permanently plug into said electrical ECG-oximeter port.

8. The device of claim 1, wherein said handheld base unit further comprises a display;
   wherein said software is configured to compute at least blood pressure results, blood oxygen level results, and graphically display electrocardiogram signal results as a function of time, and display said results on said display without interfacing with an external computerized device or remote server.

9. The device of claim 1, wherein either said external finger pulse oximeter-ECG electrode device or said handheld base unit further comprises a temperature sensor configured to monitor a body temperature of said patient.

10. The device of claim 1, wherein said device is further used to determine an effectiveness of at least one specific medication from a medication regimen comprising a plurality of medications;
   wherein said device is configured to store a plurality of individual medication impact parameters, each individual medication impact parameter providing information on how an individual known specific medication alters a specific type of pulse wave measurement;
   wherein said plurality of medication impact parameters and plurality of patient reference information further provide information associated with at least a plurality of different types of actual patient pulse wave measurements; wherein said device is further configured to store a plurality of patient reference information, each individual patient reference information providing information on a specific type of patient baseline pulse wave measurements in an absence of patient medication;
   wherein said device is further configured to store patient medication schedule information associated with at least one medication and medication dosing schedule for said patient;
   said processor further configured so that when said patient operable instrumentation is used on a patient with patient medication schedule information, obtaining a plurality of different types of actual patient pulse wave measurements at a known time, said processor analyzes said plurality of different types of actual patient pulse wave measurements at a known time, and determines which of said plurality of different types of actual patient pulse wave measurements are inconsistent with those expected patient pulse wave measurements calculated from said patient medication schedule information, said known time, said plurality of patient reference information, and said plurality of medication impact parameters;
   wherein said processor is further configured to store at least those specific medications where inconsistent findings were obtained in said memory;
   wherein said processor is further configured to determine said effectiveness and a medication adherence to the regimen, based on said inconsistent findings, and to establish or refine said effectiveness based on the medication adherence;
   wherein said effectiveness comprises an impact of said at least one specific medication on a patient's actual patient pulse wave measurements as compared to calculated expected patient pulse wave measurements for said medication regimen.

\* \* \* \* \*